United States Patent
Santiago et al.

(10) Patent No.: US 10,750,928 B2
(45) Date of Patent: Aug. 25, 2020

(54) SIMULTANEOUS EXTRACTION AND SEPARATION OF RNA AND DNA FROM SINGLE CELLS USING ELECTROPHORETIC TECHNIQUES

(71) Applicant: The Board of Trustees of the Leland Stanford Junior University, Stanford, CA (US)

(72) Inventors: Juan G Santiago, Stanford, CA (US); Hirofumi Shintaku, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 644 days.

(21) Appl. No.: 14/593,925

(22) Filed: Jan. 9, 2015

(65) Prior Publication Data

US 2015/0191717 A1    Jul. 9, 2015

Related U.S. Application Data

(60) Provisional application No. 61/925,626, filed on Jan. 9, 2014.

(51) Int. Cl.

| | | |
|---|---|---|
| C12P 19/34 | (2006.01) | |
| A61B 1/00 | (2006.01) | |
| G06T 7/254 | (2017.01) | |
| A61B 1/06 | (2006.01) | |
| G06T 7/00 | (2017.01) | |
| C12N 15/10 | (2006.01) | |
| C12Q 1/6806 | (2018.01) | |
| G01N 27/447 | (2006.01) | |
| A61B 1/05 | (2006.01) | |

(52) U.S. Cl.
CPC ........ *A61B 1/00009* (2013.01); *A61B 1/0005* (2013.01); *A61B 1/0676* (2013.01); *C12N 15/101* (2013.01); *C12Q 1/6806* (2013.01); *G01N 27/44791* (2013.01); *G06T 7/0016* (2013.01); *G06T 7/254* (2017.01); *A61B 1/05* (2013.01); *G06T 2207/10068* (2013.01); *G06T 2207/30032* (2013.01)

(58) Field of Classification Search
None
See application file for complete search history.

(56) References Cited

U.S. PATENT DOCUMENTS

| | | | |
|---|---|---|---|
| 6,783,647 B2 | 8/2004 | Culbertson et al. | |
| 7,419,575 B2 | 9/2008 | Culbertson et al. | |
| 8,372,629 B2 | 2/2013 | Southern et al. | |
| 8,846,314 B2 | 9/2014 | Chambers et al. | |
| 2002/0012971 A1 | 1/2002 | Mehta | |
| 2002/0189946 A1 | 12/2002 | Wainright et al. | |
| 2004/0180350 A1 | 9/2004 | Nalin et al. | |
| 2004/0182707 A1* | 9/2004 | Jardemark | B82Y 15/00 204/451 |
| 2007/0095669 A1* | 5/2007 | Lau | B03C 5/005 204/547 |
| 2007/0281313 A1 | 12/2007 | Taniguchi et al. | |
| 2009/0042737 A1 | 2/2009 | Katz et al. | |
| 2010/0143878 A1 | 6/2010 | Olson et al. | |
| 2010/0224494 A1* | 9/2010 | Chambers | B01D 57/02 204/549 |
| 2012/0219987 A1* | 8/2012 | Mussivand | C12M 35/02 435/40.5 |
| 2014/0014515 A1* | 1/2014 | Santiago | G01N 27/44795 204/549 |
| 2016/0160208 A1* | 6/2016 | Santiago | B01L 3/502738 204/451 |

FOREIGN PATENT DOCUMENTS

| | | |
|---|---|---|
| EP | 0320937 A2 | 6/1989 |
| EP | 2073004 A1 | 6/2009 |
| WO | 2010009415 A1 | 1/2010 |
| WO | WO2011008217 A1 | 1/2011 |
| WO | WO2012138741 A2 | 10/2012 |

OTHER PUBLICATIONS

Nashimoto, Y. et al. Measurement of gene expression from single adherent cells and spheroids collected using fast electrical lysis. Anal. Chem., vol. 79, p. 6823-6830, 2007.*
Gao, J., et al. Integration of single cell injection, cell lysis, separation and detection of intracellular constituents on a microfluidic chip. Lab Chip, vol. 4, p. 47-52, 2004.*
PCT/US15/10884 International Search Report.
Kalisky et al. (2011) Genomic analysis at the single-cell level. Annu. Rev. Genet. 45:431-445.
Zare et al. (2010) Microfluidic platforms for single-cell analysis. Annu. Rev. Biomed. Eng. 12:187-201.
Marcus et al. (2006) Microfluidic single-cell mRNA isolation and analysis. Anal Chem. 78(9):3084-3089.
White et al. (2011) High-throughput microfluidic single-cell RT-qPCR. Proc. Natl. Acad. Sci. U.S.A. 108(34):13999-4004.
Zhong et al. (2008) A microfluidic processor for gene expression profiling of single human embryonic stem cells. Lab Chip. 8(1):68-74.

(Continued)

*Primary Examiner* — Kenneth R Horlick
(74) *Attorney, Agent, or Firm* — Crawford Maunu PLLC

(57) ABSTRACT

Devices and methods for preparing RNA and DNA from single cells are disclosed. In particular, the invention relates to a method of simultaneously extracting RNA and DNA from single cells and separating the nucleic acids electrophoretically. An electric field is used to lyse a single target cell, such that the plasma membrane is selectively disrupted without lysing the nuclear membrane. Cytoplasmic RNA is separated from the nucleus by performing isotachophoresis (ITP) in the presence of a sieving matrix that preferentially reduces the mobility of the nucleus. During ITP, the cytoplasmic RNA accumulates at an ITP interface between leading and trailing electrolytes and can later be extracted free of nuclear DNA. The method can be performed in a microfluidic device that fully automates all steps of the process.

59 Claims, 22 Drawing Sheets

(56) References Cited

OTHER PUBLICATIONS

Borland et al. (2008) Chemical analysis of single cells. Annu. Rev. Anal. Chem. 1:191-227.
Han et al. (2000) In-situ sampling and separation of RNA from individual mammalian cells. Anal. Chem. 72(17):4073-4079.
Schmid et al. (2010) Chemical and biological single cell analysis. Curr. Opin. Biotechnol. 21(1):12-20.
McClain et al. (2003) Microfluidic devices for the high-throughput chemical analysis of cells. Anal. Chem. 75:5646-5655.
Sims et al. (2007) Analysis of single mammalian cells on-chip. Lab Chip 7:423-440.
EPO. Supplementary European Search Report dated Jul. 3, 2017, for related European Patent Application No. 15735437.4 (2 pages).
Chien-Hsuan Tai et al. "Automatic microfluidic platform for cell separation and nucleus collection." Biomedical Microdevices, vol. 9, No. 4, pp. 533-543 (May 17, 2007).
Anita Rogacs et al. "Purification of nucleic acids using isotachophoresis." Journal of Chromatography A, vol. 1335, pp. 105-120 (Dec. 15, 2013).
Hirofumi Shintaku et al. "On-Chip Separation and Analysis of RNA and DNA from Single Cells." Anal. Chem., vol. 86, No. 4, pp. 1953-1957 (Feb. 18, 2014).

\* cited by examiner

SIMULTANEOUS EXTRACTION AND SEPARATION OF RNA AND DNA FROM SINGLE CELLS USING ELECTROPHORETIC TECHNIQUES

CROSS-REFERENCE TO RELATED APPLICATION

This application claims benefit under 35 U.S.C. § 119(e) of provisional application 61/925,626, filed Jan. 9, 2014, which is hereby incorporated by reference in its entirety.

TECHNICAL FIELD

The present invention pertains generally to devices and methods for preparing RNA and DNA. In particular, the invention relates to a method of simultaneously extracting RNA and DNA from a single cell using selective cell lysis and isotachophoresis.

BACKGROUND

RNA and DNA analysis at the single cell level is crucial to the understanding of the heterogeneity within cell populations, and new tools for this work are just emerging (Kalisky et al. (2011) Annu. Rev. Genet. 45:431-445). Recent progress in microfluidics has revolutionized the area and created new capabilities for single cell analysis (Zare et al. (2010) Annu. Rev. Biomed. Eng. 12:187-201). For example, Marcus et al. (Analytical Chemistry (2006) 78:956-958) demonstrated an integrated microfluidic chip that performed single cell lysis, RNA purification, and complementary DNA (cDNA) synthesis. Since then, the technique has been improved (White et al. (2011) Proc. Natl. Acad. Sci. USA 108:13999-14004), and similar techniques have been used to measure single cells (thong et al. (2008) Lab on a Chip 8:68-74). The technique is now well established but requires a specialized system (e.g., pumping liquids and valving). Further, the basic idea of quantifying the amount of RNA has relied upon its conversion to cDNA and subsequent amplification by enzymatic processes such as quantitative polymerase chain reaction (qPCR). Such basic approaches are effective, but may not be optimal, as PCR is well-known to introduce sequence-specific bias (Kalisky et al., supra). Because of this, most findings require validation by in situ hybridization or staining.

Capillary electrophoresis (CE) methods using either traditional free-standing capillaries or on-chip CE have also been used for handling and analyzing molecules from single cells (Borland et al. (2008) Annu. Rev. Anal. Chem. 1:191-227). However, few studies have focused on direct detection of RNA without amplification. Han and Lillard (Anal. Chem. (2000) 72:4073-4079) demonstrated direct measurement of RNA from a single cell and obtained an electropherogram of ribosomal RNA. They performed cell lysis inside the same capillary used for separation using sodium dodecyl sulfate (SDS). Their protocol separated RNA by CE and quantified RNA using an ethidium bromide label and laser-induced fluorescence detection. In subsequent work, Lillard's group examined RNA expression in various phases of the cell cycle (G1, S, G2, and M) and reported changes of total amount of RNA and individual RNA sequences over each phase (Han & Lillard (2002) Anal. Biochem. 302:136-143). Their limit of detection for CE was well below the single cell level. However, their protocol provided only the relative amount of the RNA, and no simultaneous RNA and DNA information.

Thus, there remains a need for better methods of extracting and measuring total cytoplasmic RNA and nuclear DNA from single cells.

SUMMARY

The present invention is based, in part, on the discovery of a new method for simultaneously preparing RNA and DNA from a single cell. In particular, the method utilizes an electric field to selectively lyse the plasma membrane of a cell and isotachophoresis to separate cytoplasmic RNA from the nucleus.

In one embodiment, the invention includes a method of preparing RNA and DNA from a cell, the method comprising: a) isolating the cell in a fluidic channel; b) applying an electric field to the fluidic channel, whereby the plasma membrane of the cell is lysed without disrupting the nuclear membrane; and c) performing isotachophoresis (ITP) on the contents of the cell using: i) a trailing electrolyte (TE) and a leading electrolyte (LE), wherein cytoplasmic RNA is concentrated at the LE-TE interface, and ii) a sieving matrix that retards the nucleus, whereby cytoplasmic RNA is separated from nuclear DNA of the cell. The fluidic channel may be an etched channel in a microfluidic device or a capillary tube. In one embodiment, the electric field is applied to the fluidic channel by generating a bipolar voltage pulse that disrupts the plasma membrane of the cell. After performing ITP, the method may further comprise removing the nucleus from the fluidic channel, removing the cytoplasmic RNA from the LE-TE interface, and/or removing cell debris from the cytoplasmic RNA.

In another embodiment, the invention includes a method of preparing nuclear RNA and cytoplasmic RNA from a cell, the method comprising: a) isolating the cell in a fluidic channel; b) applying an electric field to the fluidic channel, whereby the plasma membrane of the cell is lysed without disrupting the nuclear membrane; and c) performing isotachophoresis (ITP) on the contents of the cell using: i) a trailing electrolyte (TE) and a leading electrolyte (LE), wherein cytoplasmic RNA is concentrated at the LE-TE interface, and ii) a sieving matrix that retards the nucleus, whereby cytoplasmic RNA is separated from nuclear RNA contained in the nucleus. In certain embodiments, the method further comprises isolating the nuclear RNA from the nucleus. In one embodiment, nuclear DNA is removed by digesting the DNA enzymatically (e.g., with a deoxyribonuclease).

In certain embodiments, the sieving matrix comprises a block copolymer, a linear polymer, or a cross-linked polymer. In one embodiment, the sieving matrix comprises polyvinylpyrrolidone (PVP) at a concentration greater than 0.2%. In one embodiment, the concentration of PVP is about 0.4%.

In certain embodiments, ITP is performed with the LE and TE in solution at a pH between 4 and 10. In one embodiment, the pH is between about 8.0 and about 8.3. For example, ITP can be performed with a solution containing the LE comprising Tris and HCl and a solution containing the TE comprising Tris and HEPES (see Example 1).

In another embodiment, the method further comprises adding an agent for suppressing electroosmotic flow in the fluidic channel. Agents for suppressing electroosmotic flow include, but are not limited to polylactams, substituted polyacrylamide derivatives, water soluble methylhydroxyethyl derivatives of cellulose, polyvinylalcohol, polyvinylpyrrolidones, and polyethyleneglycols. In one embodiment, the polylactam is polyvinylpyrrolidone.

In another embodiment, the method further comprises adding an osmotic agent to compensate for differences in osmotic pressure between intracellular and extracellular media. In one embodiment, the osmotic agent is sucrose.

In another embodiment, the method further comprises lysing the nuclear membrane of the nucleus. The nuclear membrane can be lysed using any chemical, mechanical, electrical, or thermal lysing method.

In another embodiment, the method further comprises adding a detectable label to the RNA or DNA. In one embodiment, the detectable label is a fluorescent dye.

The methods of the invention can be used to prepare DNA and RNA from any cell from any prokaryotic or eukaryotic organism, including bacteria, fungi, plants, protists, or animals. The cell can be from a biological sample containing cells, such as a tissue or bodily fluid, including but not limited to, blood, saliva, cells from buccal swabbing, fecal matter, urine, bone marrow, spinal fluid, lymph fluid, skin, organs, and biopsies, or in vitro cell culture constituents, including recombinant cells and tissues grown in culture medium.

The procedures described herein may be used alone or in combination with any other method for isolating or purifying nucleic acids (e.g., RNA or DNA). For example, individual nucleic acids may be further purified by immobilization on a solid support such as, but not limited to, adsorbent beads, magnetic beads, or silica, or by gel filtration, reverse phase, ion exchange, or affinity chromatography. Alternatively, an electric field-based method can be used to separate the desired nucleic acid molecule from other molecules. Exemplary electric field-based methods include polyacrylamide gel electrophoresis, agarose gel electrophoresis, capillary electrophoresis, and pulsed field electrophoresis.

In another embodiment, the method further comprises quantifying the amount of cytoplasmic RNA, nuclear RNA, or nuclear DNA extracted from the cell.

In another embodiment, the method further comprises amplifying at least one RNA or DNA molecule.

The methods described herein can be performed in a microfluidic device that fully automates all steps of the process. See, e.g., Example 1 and FIGS. 1A-1C, 3A, and 3B for a description of an exemplary microfluidic device. In one embodiment, the microfluidic device comprises at least a first fluidic channel and a second fluidic channel connected at a junction, wherein each fluidic channel has a first end connected to a first reservoir and a second end connected to a second reservoir. DNA and RNA can be prepared from a biological sample comprising cells using such a device by a method comprising: a) filling the first channel with a solution comprising a leading electrolyte and a sieving matrix; b) isolating a cell in the first channel by introducing a sample comprising cells into the first reservoir of the first channel and applying a vacuum at a reservoir of the second channel to move a single cell into the first channel, thereby isolating the cell; c) applying an electric field across the first channel in the vicinity of the single cell, whereby the plasma membrane of the single cell is lysed without disrupting the nuclear membrane; d) adding a trailing electrolyte to the first reservoir of the first channel; and e) performing isotachophoresis (ITP) on the contents of the single cell in the first channel. In certain embodiments, the method further comprises delivery of the nucleus and cytoplasmic RNA to separate locations in the device. For example, the nucleus and cytoplasmic RNA may be distributed to separate reservoirs or channels within the device. In one embodiment, the first fluidic channel of the device divides at at least one channel branch point into two or more channels, wherein the nucleus and cytoplasmic RNA are distributed to separate channels. Additionally, the contents of the cell (e.g., nucleic acids, proteins, lipids, small molecules, etc.) may be further fractionated and distributed to various separate channels or reservoirs.

These and other embodiments of the subject invention will readily occur to those of skill in the art in view of the disclosure herein.

BRIEF DESCRIPTION OF THE FIGURES

FIG. 1A shows single cells introduced from the W reservoir and isolated in the injection channel by applying a vacuum. FIG. 1B shows that each cell was electrically lysed by a bipolar voltage pulse applied between the N and the W reservoirs. FIG. 1C shows that total cytoplasmic RNA from the lysed cell was extracted and accumulated within the ITP interface. Remaining cell debris (including the nucleus) was separated from the RNA. FIG. 1D shows a bright field image of an isolated single cell in the injection channel. FIG. 1E shows lysing of individual cells. Cells 1 and 2 are respectively within and outside the lysing electric field. Only cell 1 is lysed. FIG. 1F shows typical experimental images of the cell nucleus (left behind) and extracted RNA from a single cell at the ITP interface.

FIGS. 2A-2C summarize data from our method, and FIGS. 2D-2F show FACS data for comparison. FIG. 2A shows a histogram of the absolute amount of extracted RNA masses. FIG. 2B shows a histogram of relative amount of DNA. FIG. 2C shows the relationship between the absolute amount of RNA and the relative amount of DNA from living single cells. The contour lines show the result of two-dimensional Gaussian analysis. FIG. 2D shows a histogram of relative amount of RNA by FACS. FIG. 2E shows a histogram of the relative amount of DNA by FACS. FIG. 2F shows the contour lines showing the correlation between RNA and DNA.

FIG. 8A shows a two dimensional fluorescence image of a nucleus. FIG. 8B shows the spatial distribution of fluorescence intensity along line X-X' and the threshold for dissection.

FIG. 9A shows fitting with two two-dimensional Gaussian distributions. FIG. 9B shows fitting with three two-dimensional Gaussian distributions.

DETAILED DESCRIPTION

Figure 1A:
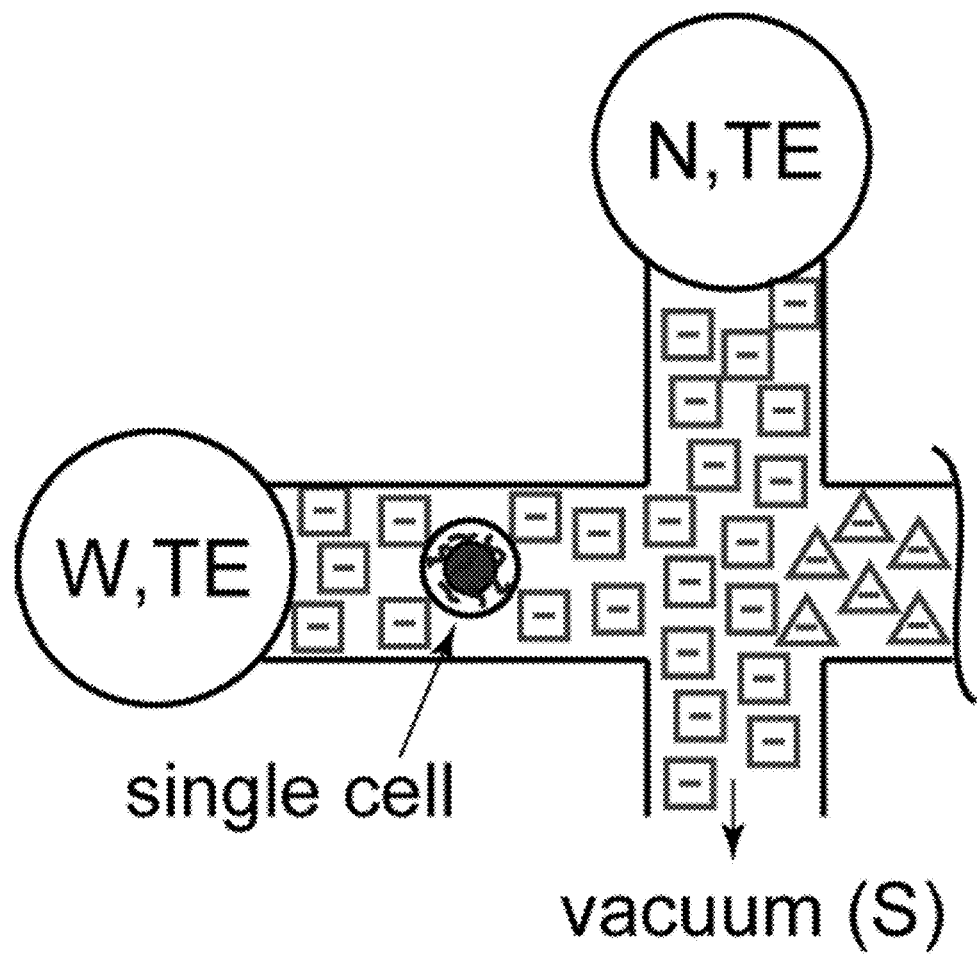
FIGS. 1A-1F show a schematic of the single cell RNA extraction and quantification method.

The practice of the present invention will employ, unless otherwise indicated, conventional methods of chemistry, biochemistry, cell biology, molecular biology and recombinant DNA techniques, within the skill of the art. Such techniques are explained fully in the literature. See, e.g., *Single Cell Analysis: Technologies and Applications* (D. Anselmetti ed., Wiley-Blackwell, 2009); T. K. Khurana *On-chip isotachophoresis assays for high sensitivity electrophoretic preconcentration, separation, and indirect detection* (ProQuest, UMI Dissertation Publishing, 2011); F. M. Everaerts, J. L. Beckers *Isotachophoresis Theory, Instrumentation and Applications* (Journal of chromatography library, Volume 6, Elsevier Science Ltd., 1976); A. L. Lehninger, *Biochemistry* (Worth Publishers, Inc., current addition); Sambrook et al., *Molecular Cloning: A Laboratory Manual* ($3^{rd}$ Edition, 2001); *RNA: Methods and Protocols* (Methods in Molecular Biology, edited by H. Nielsen, Humana Press, $1^{st}$ edition, 2010); Rio et al. *RNA: A Laboratory Manual* (Cold Spring Harbor Laboratory Press; $1^{st}$ edition, 2010); Farrell *RNA Methodologies: Laboratory Guide for Isolation and Characterization* (Academic Press; $4^{th}$ edition, 2009); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "an RNA" includes a mixture of two or more RNA molecules, and the like.

As used herein, the term "biological sample" includes any cell or tissue or bodily fluid containing cells from a prokaryotic or eukaryotic organism, such as cells from bacteria, fungi, protists, plants, and animals. The biological sample may include cells from a tissue or bodily fluid, including but not limited to, blood, saliva, cells from buccal swabbing, fecal matter, urine, bone marrow, spinal fluid, lymph fluid, skin, organs, and biopsies, as well as in vitro cell culture constituents, including recombinant cells and tissues grown in culture medium.

The term "electroosmotic flow" refers to the motion of liquid induced by an applied potential across a porous material, capillary tube, microchannel, or other fluid conduit.

The term "about," particularly in reference to a given quantity, is meant to encompass deviations of plus or minus five percent.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a new method for simultaneously preparing RNA and DNA from single cells. In particular, a single cell is isolated from a sample, and an electric field is used to lyse the cell, such that the plasma membrane is selectively disrupted without lysing the nuclear membrane. Cytoplasmic RNA is separated from the nucleus by performing isotachophoresis (ITP) in the presence of a sieving matrix that preferentially reduces the mobility of the nucleus. During ITP, the cytoplasmic RNA accumulates at an ITP interface between leading and trailing electrolytes and can later be extracted free of nuclear DNA. The method can be performed in a microfluidic device that fully automates all steps of the process (see Example 1).

In order to further an understanding of the invention, a more detailed discussion is provided below regarding this novel method of preparing RNA and DNA.

The present isotachophoresis methods are used for simultaneous extraction of DNA and RNA from a single cell. First, a single cell is isolated in a fluidic channel. The single cell can be isolated from a biological sample comprising other cells by appropriate dilution of the sample and injection of the cell in a small isolation volume into the fluidic channel. The cell can be moved into the channel by any suitable means, such as by applying pressure or vacuum to draw the cell into the channel. Next, an electric field is applied across the channel in the vicinity of the cell to selectively lyse the plasma membrane without disrupting the nuclear membrane. As described in Example 1, the electric field can be applied to the fluidic channel by generating a bipolar voltage pulse that selectively disrupts the plasma membrane of the cell. Then, ITP is performed on the contents of the cell with trailing and leading electrolytes that are selected such that the cytoplasmic RNA focuses at the TE-LE interface. Preferably, the TE and LE are chosen such that contaminating species (e.g., lysed cell membrane, proteins, etc.) have electrophoretic mobilities either smaller than the trailing ion or larger than the leading ion and are not focused at the TE-LE interface with the cytoplasmic RNA. In order to separate cytoplasmic RNA from the nucleus, ITP is performed in the presence of a sieving matrix, which retards the nucleus and prevents it from focusing at the TE-LE interface. After ITP, the nucleus and the cytoplasmic RNA can be separately removed from the fluidic channel and further processed if desired for downstream applications.

In a variation of the method, isotachophoresis is used for simultaneous extraction of nuclear RNA and cytoplasmic RNA from a single cell. Similarly, a cell is isolated in a fluidic channel and an electric field is applied to the fluidic channel, whereby the plasma membrane of the cell is lysed without disrupting the nuclear membrane. Isotachophoresis is performed on the contents of the cell in the presence of a sieving matrix that retards the nucleus, whereby cytoplasmic RNA is separated from nuclear RNA contained in the nucleus. In certain embodiments, the method further comprises isolating the nuclear RNA from the nucleus. Nuclear DNA can be removed from the nuclear RNA, for example, by digesting the DNA enzymatically (e.g., with a deoxyribonuclease).

The methods of the invention can be used to prepare DNA and RNA from any cell from any prokaryotic or eukaryotic organism, including bacteria, fungi, plants, protists, or animals. The cell can be from a biological sample containing cells, such as a tissue or bodily fluid, including but not limited to, blood, saliva, cells from buccal swabbing, fecal matter, urine, bone marrow, spinal fluid, lymph fluid, skin, organs, and biopsies, or in vitro cell culture constituents, including recombinant cells and tissues grown in culture medium. The methods can be applied to living cells or fixed cells.

In certain embodiments, the fluidic channel is an etched channel in a microfluidic device or a capillary tube. The channel may be composed of a non-conducting material, such as silicate or borosilicate. The channel may be treated for electroosmotic flow suppression or for other beneficial flow modifying effects. For example, the channel may be pretreated with one or more agents including silanizing agents, alcohols, acids, or water.

Figure 3A:
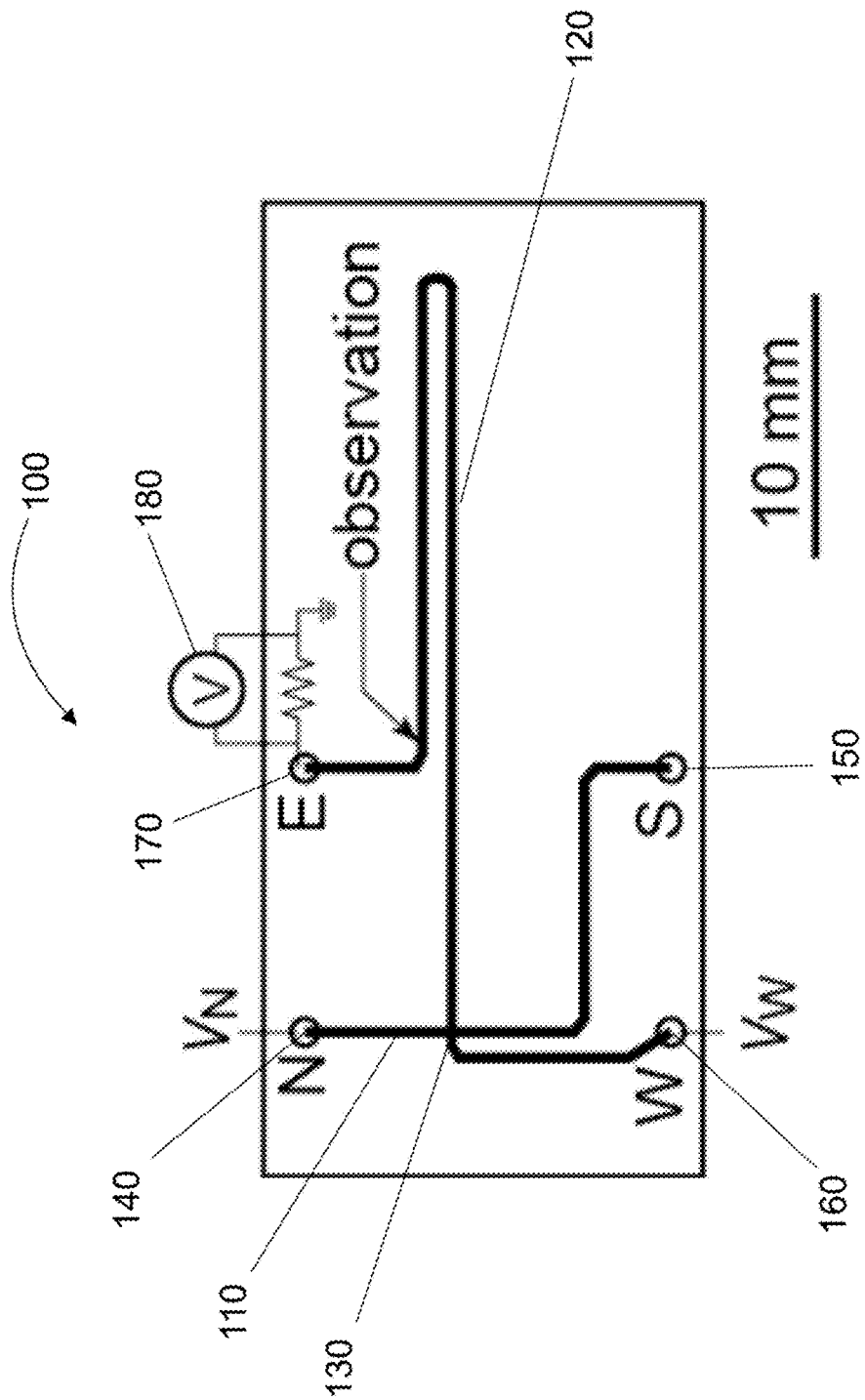
FIG. 3A shows the microfluidic chip geometry. To measure the current during the ITP process, we connected in series an input of a DAQ (NI USB-6009, National instruments) to the electrode placed in the S reservoir. We estimated the current by dividing the voltage by the input resistance, 144 k$\Omega$, of the DAQ. The input resistance was negligibly small compared to the microchannel resistance that was approximately 100 M$\Omega$

The methods described herein can be performed in a microfluidic device that fully automates all steps of the process. An exemplary microfluidic device comprising microchannels configured in a cross geometry is described in Example 1 (see FIGS. 1A-1C, 3A, and 3B). In one embodiment, the invention includes a microfluidic device 100 comprising at least a first fluidic channel 110 and a second fluidic channel 120 connected at a junction 130, wherein each fluidic channel has a first end connected to a first reservoir and a second end connected to a second reservoir (see FIG. 3A showing a schematic of such a device comprising 4 reservoirs with a N reservoir 140 and S reservoir 150 connected to the first fluidic channel 110 and a W reservoir 160 and E reservoir 170 connected to the second fluidic channel 120). A voltage source 180 can be connected to the device to apply an electric field across a channel.

In certain embodiments, the microfluidic device is designed to allow delivery of the nucleus and cytoplasmic RNA to separate locations in the device. In one embodiment, the fluidic channel, where the nucleus and cytoplasmic RNA are isotachophoretically separated, comprises one or more channel branch points where the channel divides into two or more channels allowing the nucleus and cytoplasmic RNA to be distributed to separate channels. Additionally, the device may comprise one or more additional channels or reservoirs to allow other components of the cell (e.g., nuclear RNA, proteins, lipids, small molecules, etc.) to be fractionated and distributed to separate channels or reservoirs.

DNA and RNA can be prepared from a biological sample comprising cells using such a device by a method comprising: a) filling the first channel with a solution comprising a leading electrolyte and a sieving matrix; b) isolating a cell in the first channel by introducing a sample comprising cells into the first reservoir of the first channel and applying a vacuum at a reservoir of the second channel to move a single cell into the first channel, thereby isolating the cell; c) applying an electric field across the first channel in the vicinity of the single cell, whereby the plasma membrane of the single cell is lysed without disrupting the nuclear membrane; d) adding a trailing electrolyte to the first reservoir of the first channel; and e) performing isotachophoresis (ITP) on the contents of the single cell in the first channel. In certain embodiments, the method further comprises delivery of the nucleus and cytoplasmic RNA to separate locations in the device. For example, the nucleus and cytoplasmic RNA may be distributed to separate reservoirs or channels within the device. In one embodiment, the first fluidic channel of the device divides at at least one channel branch point into two or more channels, wherein the nucleus and cytoplasmic RNA are distributed to separate channels. Additionally, the contents of the cell (e.g., nucleic acids, proteins, lipids, small molecules, etc.) may be further fractionated and distributed to various separate channels or reservoirs.

In certain embodiments, ITP is performed with the LE and TE in solution at a pH between 4 and 10. Electrolytes may include, but are not limited to chloride ions as the LE and 6-aminocaproic acid as the TE; Tris and HCl as the LE and Tris and HEPES as the TE; 6-aminocaproic acid and HCl as the LE and 6-aminocaproic acid and caproic acid or Bis-Tris and dihydroxybenzoic acid as the TE; and Tris-HCl as the LE and glycine or TRIS-glycine as the TE. The concentrations of ions and buffers can be adjusted to provide the appropriate effective mobility. Exemplary LE and TE solutions include an LE solution containing 50 mM Tris and 25 mM HCl at pH of 8.1 and a TE solution containing 50 mM Tris and 25 mM HEPES at pH of 8.3 (see Example 1). ITP is performed in the presence of a sieving matrix to separate the cytoplasmic RNA from the nucleus and cell debris resulting from lysis. In certain embodiments, the sieving matrix comprises a block copolymer, a linear polymer, or a cross-linked polymer.

Block copolymers comprising two or more homopolymer subunits linked by covalent bonds may be used. Alternatively, homopolymer subunits may be linked by an intermediate non-repeating subunit, known as a junction block. Block copolymers, including diblock copolymers and triblock copolymers may be used. The sieving matrix may comprise linear copolymers consisting of a single main chain or branched copolymers consisting of a main chain with one or more polymeric side chains. A number of different monomers are known for use in preparing block copolymers, including isoprene and styrene. Hydrophilic polymers such as linear low-molecular-mass polyacrylamide or low molecular-weight poly(ethylene oxide) (PEO) are suitable sieving polymers. In particular, a sieving matrix comprising polyvinylpyrrolidone (PVP) at concentrations greater than 0.2% has been found to be effective in retarding migration of the nucleus (see Example 1). In one embodiment, the sieving matrix comprises PVP at a concentration of about 0.4%.

In addition, an agent for suppressing electroosmotic flow may be added to the fluidic channel. Agents for suppressing electroosmotic flow include, but are not limited to polylactams (e.g., polyvinylpyrrolidone), substituted polyacrylamide derivatives, water soluble methylhydroxyethyl derivatives of cellulose, polyvinylalcohol, polyvinylpyrrolidones, and polyethyleneglycols.

An osmotic agent (e.g., sucrose) may also be added in order to compensate for differences in osmotic pressure between intracellular and extracellular media, to preserve cell viability prior to lysis, and to keep the nucleus intact after lysis.

After performing ITP, the nuclear membrane of the nucleus may be separately lysed to extract the nuclear contents, including DNA and/or nuclear RNA. The nuclear membrane can be lysed using any chemical, mechanical, electrical, or thermal lysing method. Commonly used methods include freeze-thaw cycling, sonication, electroporation, pressure, enzymatic lysis, or mechanical disruption such as by grinding with a mortar and pestle (typically in the presence of detergent or liquid $N_2$) or using a bead beater or rotating blade. Examples of chemical lysis agents include detergents and surfactants (e.g., Triton-X-100, Igepal CA-630, and sodium dodecyl sulfate) and polyanions (e.g., heparin). Additionally, enzymatic or chemical methods may be used to remove contaminating nuclear components (e.g., protein, RNA, or other macromolecules). For example, RNA nucleases can be used to remove contaminating RNA if DNA is being isolated; DNA nucleases can be used to remove contaminating DNA if nuclear RNA is being isolated; and proteases can be used to remove contaminating proteins. A nuclease inhibitor may be used to prevent degradation of nucleic acids.

If desired, after separation of the nucleus and cytoplasmic RNA, individual nucleic acid molecules (e.g., RNA or DNA) may be isolated or purified for certain purposes using methods well-known in the art. For example, nucleic acids may be purified by immobilization on a solid support, such as silica, adsorbent beads (e.g., oligo(dT) coated beads or beads composed of polystyrene-latex, glass fibers, cellulose or silica), magnetic beads, or by reverse phase, gel filtration, ion-exchange, or affinity chromatography. Nucleic acids can also be isolated from suspensions by conventional methods, such as phenol-chloroform extraction or precipitation with alcohol. Alternatively, an electric field-based method can be used to separate the desired RNA or DNA molecule from other molecules. Exemplary electric field-based methods include polyacrylamide gel electrophoresis, agarose gel electrophoresis, capillary electrophoresis, and pulsed field electrophoresis. See, e.g., Sambrook et al., *Molecular Cloning: A Laboratory Manual* (3$^{rd}$ Edition, 2001); *RNA: Methods and Protocols* (Methods in Molecular Biology, edited by H. Nielsen, Humana Press, 1st edition, 2010); Rio et al. *RNA: A Laboratory Manual* (Cold Spring Harbor Laboratory Press; 1st edition, 2010); Farrell *RNA Methodologies: Laboratory Guide for Isolation and Characterization* (Academic Press; 4$^{th}$ edition, 2009); Zahringer (2012) Lab Times (2-2012):52-63; Garcia-Schwarz et al. (2012) Journal of Visualized Experiments 61:e3890; Hagan et al. (2009) Anal Chem. 81(13):5249-5256; Righetti (2005) J. Chromatogr. A10 79(1-2):24-40; Gebauer et al. (2011) Electrophoresis 32(1):83-89; herein incorporated by reference in their entireties.

The methods of the invention can be used for absolute quantification and analysis of RNA and DNA from a single cell. After separation, RNA and DNA molecules, prepared by the methods described herein, can be used for various purposes, including but not limited to sequencing, PCR, ligation, transcriptome analysis, microarray analysis, northern analysis, and library construction.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

On-Chip Separation and Analysis of RNA and DNA from Single Cells

We describe a technique for the extraction of RNA and DNA from single cells using electrophoretic techniques for simultaneous RNA and DNA analysis at the single cell level. A combination of on-chip electrical lysis and isotachophoresis (ITP) is used to isolate single live cells. Cells are lysed and total cytoplasmic RNA and nuclear DNA are extracted, concentrated, and measured individually, all within 5 minutes. Focusing RNA into an ITP interface makes the process robust to dispersion, and is compatible with integration with downstream analysis such as capillary electrophoresis (CE) and cDNA hybridization based assays (Bahga et al. (2011) Anal. Chem. 83:6154-6162; Eid et al. (2013) Analyst 138: 3117-3120; and Garcia-Schwarz & Santiago (2013) Angew. Chem. Int. Ed. Engl. 52(44):11534-11537).

Methods

ITP Chemistry

The leading electrolyte (LE) was 50 mM Tris and 25 mM HCl containing 0.4% poly(vinylpyrrolidone) (PVP) and 1× SYBR Green II (calculated pH of 8.1). The trailing electrolyte (TE) was 50 mM Tris and 25 mM HEPES containing (initial calculated pH of 8.3) 0.4% poly(vinylpyrrolidone) (PVP). We included PVP to both suppress electroosmotic flow and separate the extracted RNA from the cell debris via the sieving effect of PVP (see SI section S-2 for selection of appropriate PVP concentration). We obtained Tris, HEPES, and HCl from Sigma-Aldrich (St. Louis, Mo.); and SYBR Green II from Invitrogen (Carlsbad, Calif.); and PVP (MW 1 MDa) from ACROS Organics (Thermo Fisher Scientific, N.J.). We prepared all solutions in UltraPure DNase-/RNase-free deionized (DI) water (GIBCO Invitrogen, Carlsbad, CA).

Cell Preparation

We cultured the A20 cell line (mouse lymphocyte cells) in RPMI-1640 Medium (GIBCO) with 10% fetal bovine serum (GIBCO) and 1% penicillin-streptomycin-glutamine (GIBCO) at 37° C. in 5% $CO_2$. We washed the cells with phosphate buffered saline once and suspended in a sample buffer solution containing 50 mM Tris, 25 mM HEPES, and 175 mM sucrose at the concentration of about 5 cells/μL and stored on ice until experiments. We added 175 mM sucrose to the sample buffer to compensate the osmotic pressure and to preserve the cell viability until the lysis. We confirmed the sample buffer did not have significant adverse effect on cell viability for at least 3 hours (see FIG. 4). In all cases, we used cell samples prepared within 3 hours or less.

Channel Preparation

FIG. 3A shows the geometry of the microfluidic chip. Prior to each experiment, we preconditioned the microchannel by filling E and S reservoirs, and applying vacuum at N and W reservoirs using a single split vacuum line. We used the following cleaning chemistry: 1 M NaOH for 10 minutes, deionized (DI) water for 3 minutes, and then dried by applying vacuum to the W and N reservoirs for 1 minutes.

Following this, we filled the E and S reservoirs with the LE solution and applied vacuum at the N and W reservoirs to fill the microchannel for approximately 1.5 minutes. We emptied the N and W reservoirs with a vacuum line, and pipetted 2 μL of the sample solution including cells in the W reservoir and 20 μL of the TE solution in the N reservoir. We then applied a vacuum to the S reservoir to isolate a single cell in the injection channel. Once we isolated the single cell in the injection channel, we removed the vacuum and immediately put the 20 μL of the TE solution in the W reservoir.

Visualization

We performed on-chip visualizations of the extracted RNA using an inverted epifluorescence microscope (Eclipse TS100, Nikon) equipped with a 20× (UPlanFl); a blue LED (LEDC7, Thor Laboratories, Newton, N.J.); a filter cube (XF23, Omega optical, Vt.); and 0.6× demagnification lens (TV Lens C-0.6×, Nikon). We acquired images with a CCD camera (MicroMAX-1300Y, Princeton Instruments) with 100 ms exposure time and 2×2 binning.

Cell Electrical Lysis

We introduced a single cell from the W reservoir into the injection channel, where it is between the W reservoir and the cross, by applying a vacuum to the S reservoir. The length of the injection channel is 7.38 mm. The length between the N reservoir and the cross is 3.925 mm. Taking advantage of the relatively short length between the N and the W reservoirs, we applied a bipolar voltage pulse between N and W to give a high intense electric field. We electrically and selectively lysed the single cell isolated in the injection channel within 10 ms. (See the multimedia SI for the high speed observation of cell lysing process.)

Protocol of FACS Analysis

A20 cells were fixed by 70% ethanol at about 23° C. for 16 hours. Fixed cells were washed once and stained for 45 minutes at 37° C. with Hoechst 33342 (20 μg/ml, Sigma-Aldrich) in HBSS plus 2% FBS. Pyronin Y (1 μg/ml, Sigma-Aldrich) was then added to the staining solution and the cells were incubated 15 minutes at 37° C. All samples were analyzed by LSR-II-UV flow cytometer (BD Bioscience) at the Stanford Shared FACS facility.

Supplementary Methods

S-1 Electrical Lysis of Single Cells

On-chip electrical lysis was first demonstrated by MacClain et al. (Anal. Chem. (2003) 75:5646-5655) using an AC electric field of 75 Hz and 900 Vcm$^{-1}$ with a DC offset of 675 Vcm$^{-1}$. There has been a wide variety of on-chip electrical lysis. For example, Gao et al. (Lab on a Chip (2004) 4:47-52) and Munce et al. (Anal. Chem. (2004) 76:4983-4989) demonstrated electrical cell lysis with relatively lower DC electric fields using assistance of a high pH buffer (pH=9.2) and mechanical shear induced by cell trapping micro-structures, respectively. These studies used a saline-based buffer having high salt concentration (order 100 mM) to compensate the cell osmotic pressure. Here, we provide ITP chemistry using sucrose to increase osmolarity while achieving a cell lysis buffer compatible with ITP (see FIG. 4).

Figure 3B:
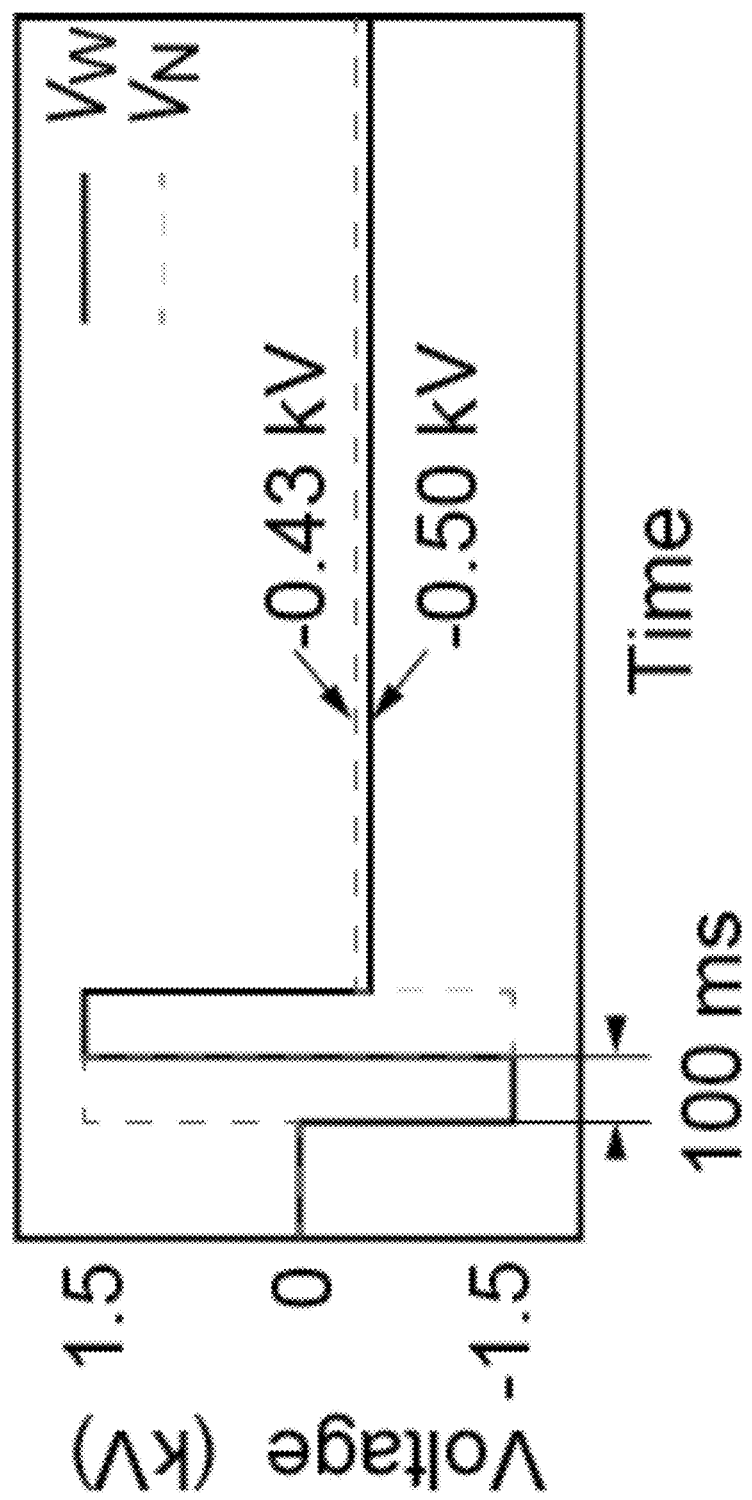
FIG. 3B shows the voltage sequence for electrical lysis and ITP.

FIG. 3B shows the voltage sequence for electrical lysis followed by ITP. We used a bipolar pulse with two individual pulses, each of a duration of 100 ms. The bipolar nature of the pulse helped minimize movement of the cell during lysing, which aided visualization of lysing. We then immediately applied potential to initiate ITP and extract RNA from the lysed cell by switching voltages $V_W$ and $V_N$ to DC voltages.

Figure 1B:
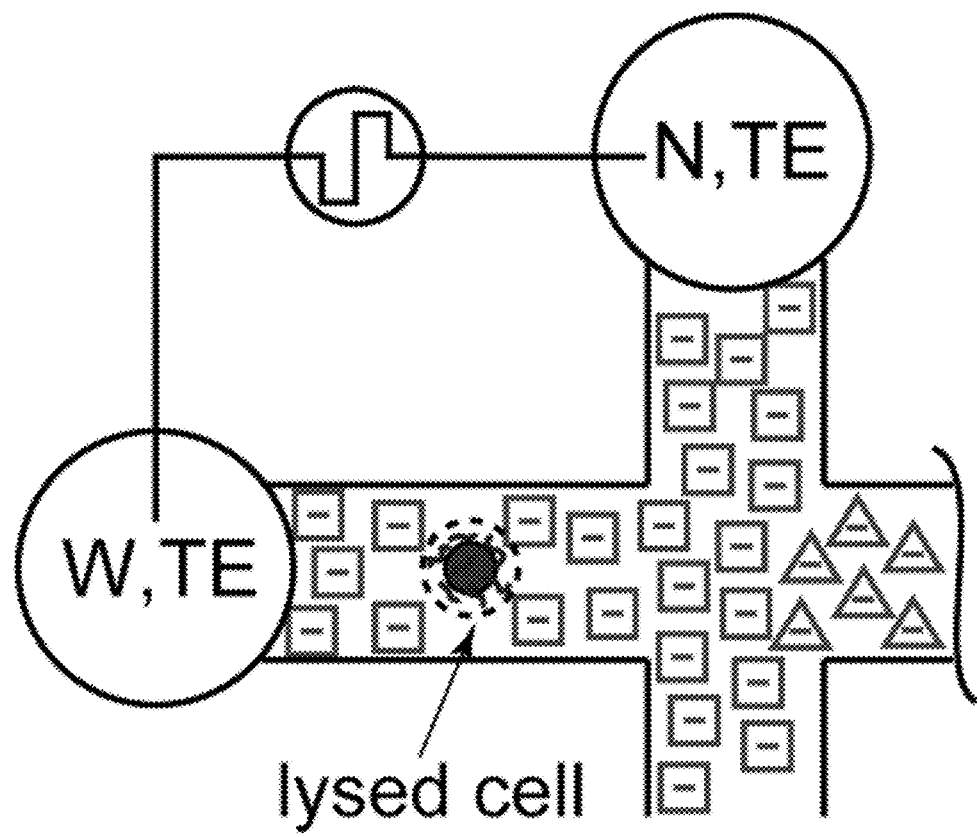
Figure 1C:
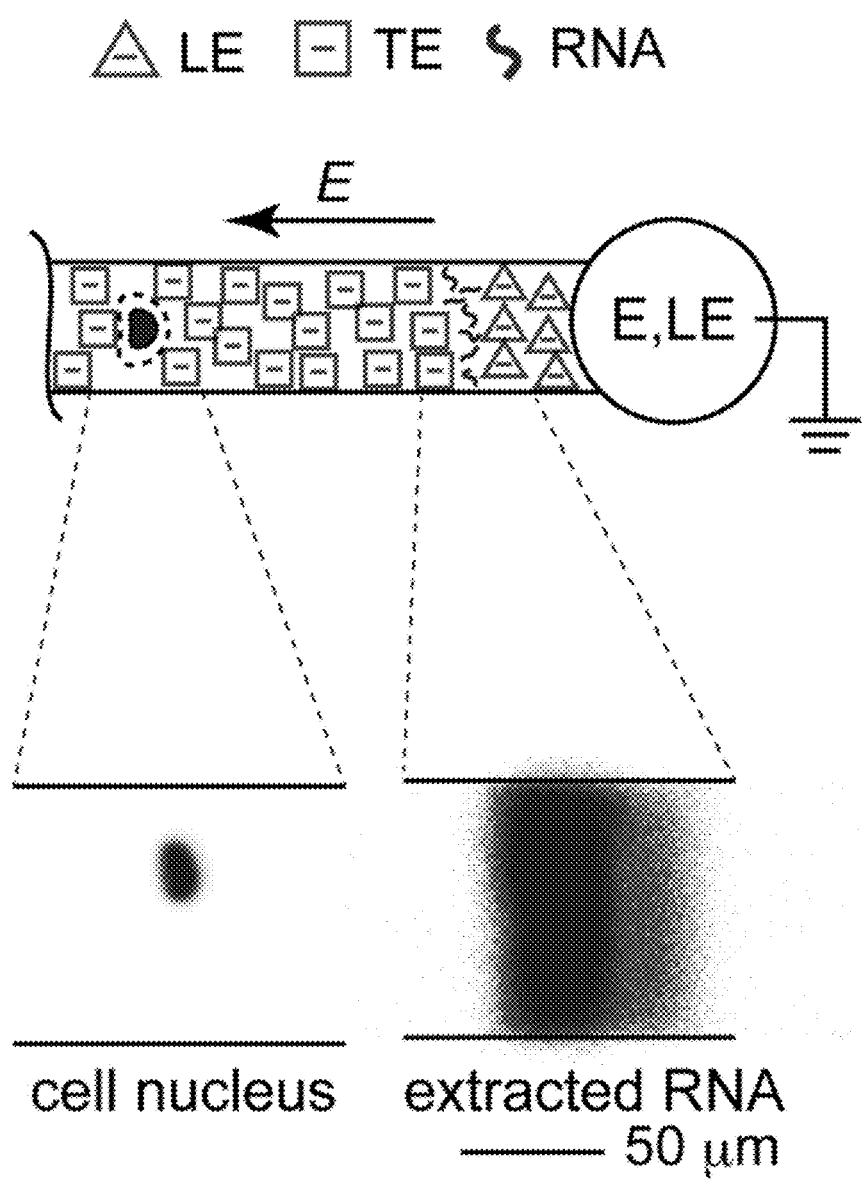
Figure 1D:
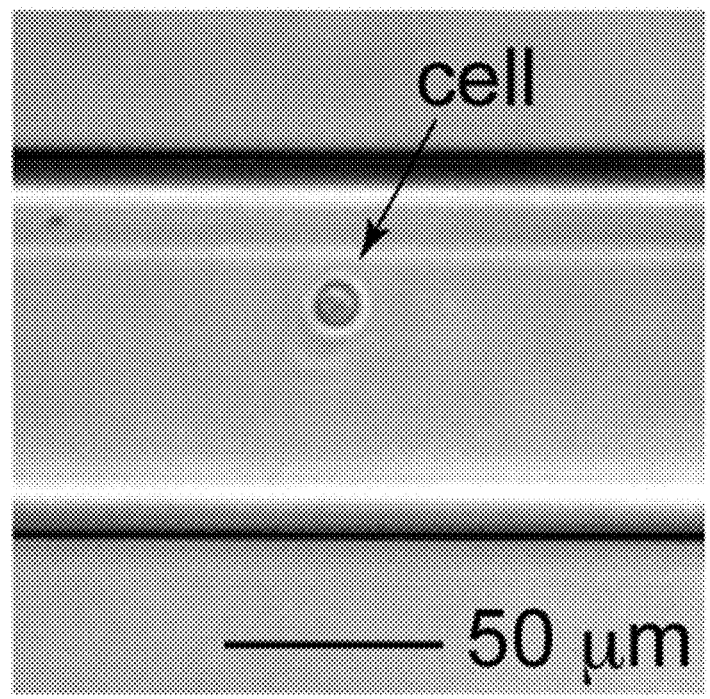
Figure 1E:
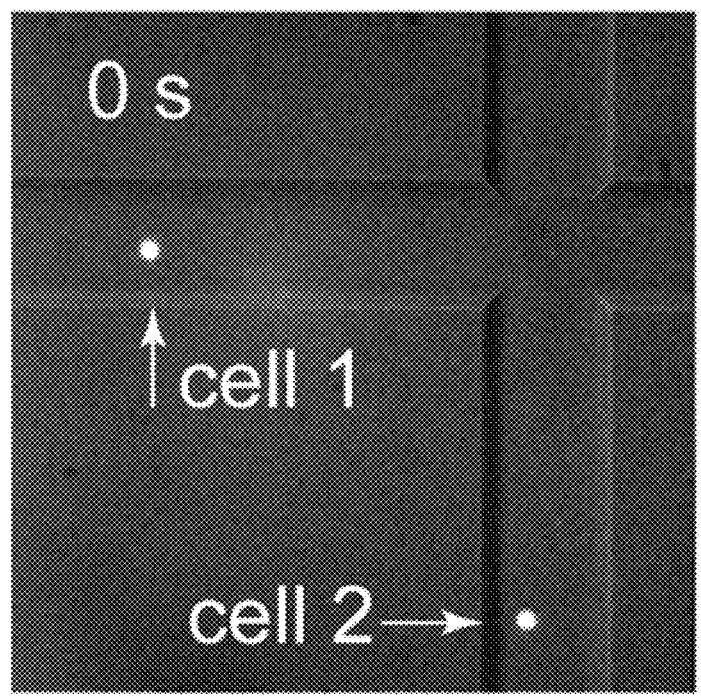
Figure 4:
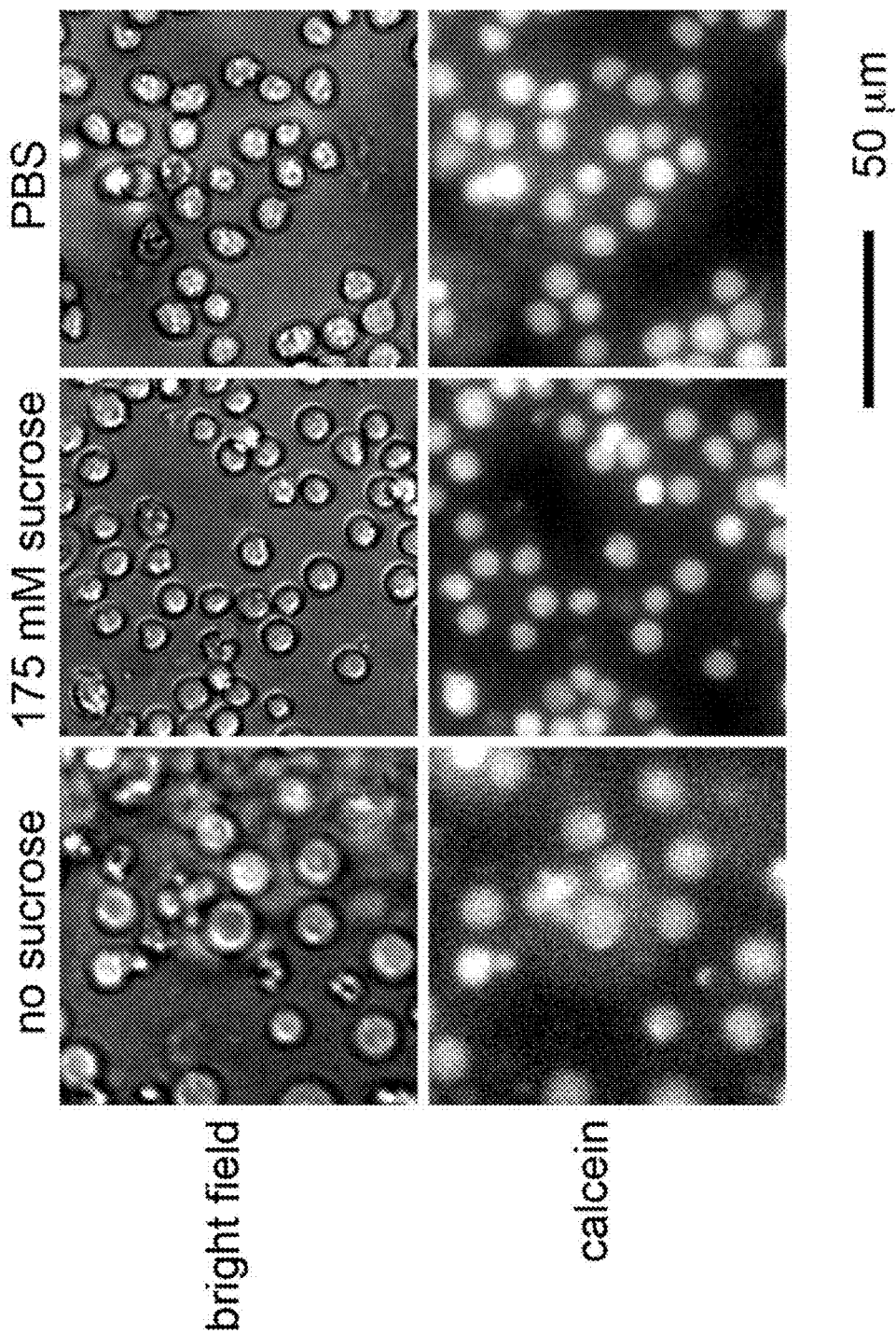
FIG. 4 shows bright field (top) and fluorescence microscopy images (bottom) of A20 cells suspended in the following three buffers: 50 mM Tris and 25 mM HEPES (left); 50 mM Tris, 25 mM HEPES and 175 mM sucrose (middle); the PBS (right). We dyed the cells with calcein to examine the cell viability. The cells suspended in the buffer with sucrose showed similar morphology with those in the PBS, indicating successful compensation of the osmotic pressure.

For the demonstration of FIG. 1D, we used cells dyed with calcein (Calcein AM 8011, Biotium, Inc) to visualize membrane permeability (see also FIG. 4). Both cells initially showed fluorescence due to the calcein. Cells exposed to the pulsed electric field (cell 1) quickly lost fluorescence in the subsequent frame, consistent with disruption of the cell membrane. In contrast, cells located in a channel branch outside the electric field (cell 2 between the junction and the S reservoir) maintained fluorescence and remained intact. This selective lysing was important to avoid contamination from non-targeted cells.

We performed highly temporally resolved imaging of electrical lysing of single cells with a high-speed camera (Phantom Micro-4M, Vision Research). These images showed disruption of the cell membrane within 10 ms (see the multimedia SI for a high frame rate movie). We estimated the electric field in the injection channel as 270 kV/m. From the characteristic 14 μm diameter of cells, we therefore estimated the potentials induced across the cell membrane were on the order of about 3 V. This was high enough compared to the typical approximately 1 V break down voltage of cell membranes.

S-2 Selection of PVP Concentration to Isolate RNA

We observed two (fluorescent) nucleic acid regions in all single cell experiments. The first was a high-mobility zone that always focused in the ITP interface. We attributed this to total cytoplasmic RNA. The second region was a roughly ellipsoidal body with characteristic major and minor radii of roughly 8 and 10 μm (see FIG. 1F). The second region focused in the ITP interface only for PVP concentrations of about 0.2% or less. At higher PVP concentrations, the second region never focused in the ITP interface. We attributed the second region to cell nuclei. After a series of preliminary experiments, we determined that 0.4% PVP concentrations sufficiently and repeatedly arrested the motion of the cell nuclei so that they never co-focused in the ITP interface. See the multimedia SI for additional information, including visualizations of separations and focusing at low and high PVP.

Figure 5:
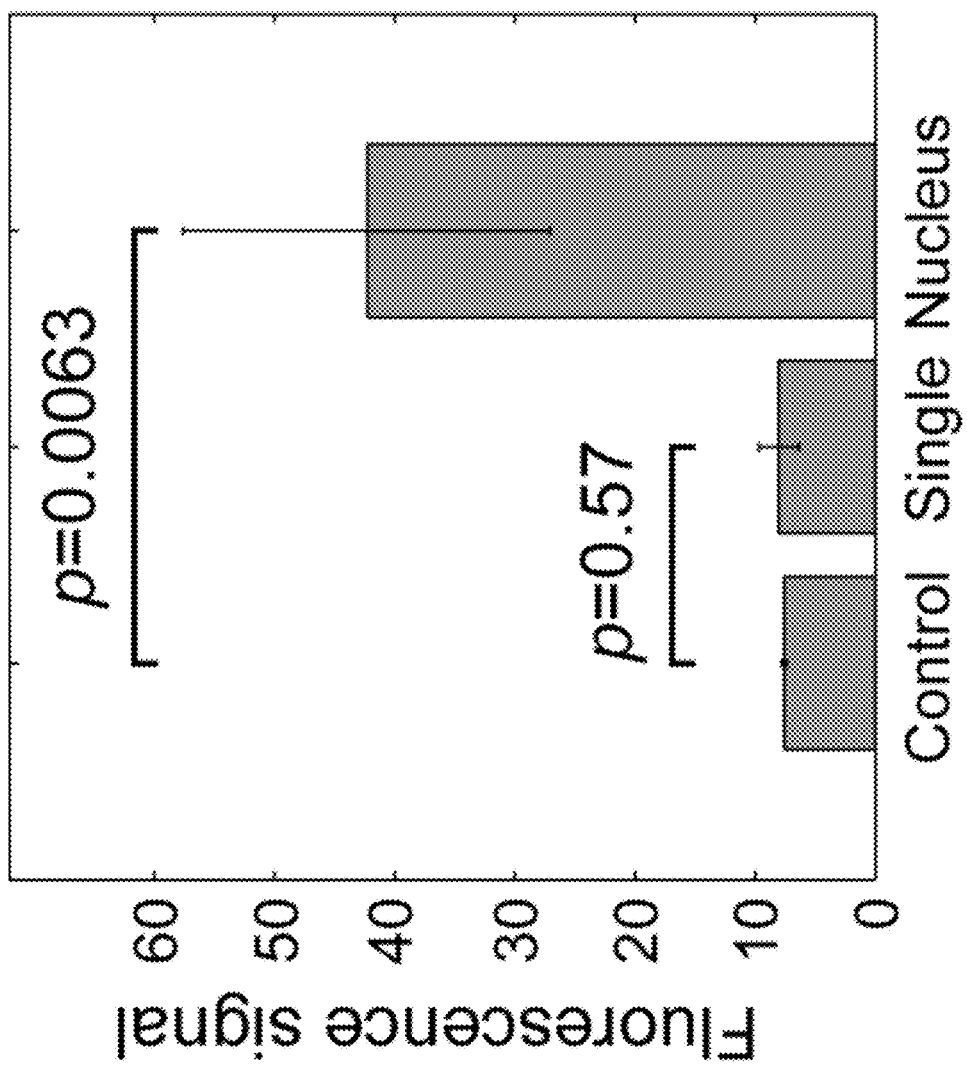
FIG. 5 shows the fluorescence signal of the ITP interface visualized with Hoechst 33342 of the DNA specific dye. The signal with a single cell showed no significant difference from that of the control (p=0.57). The nucleus showed significantly high fluorescence signal compared to the control (p=0.0063). We concluded that the DNA extracted to the ITP interface was negligible.
Figure 6:
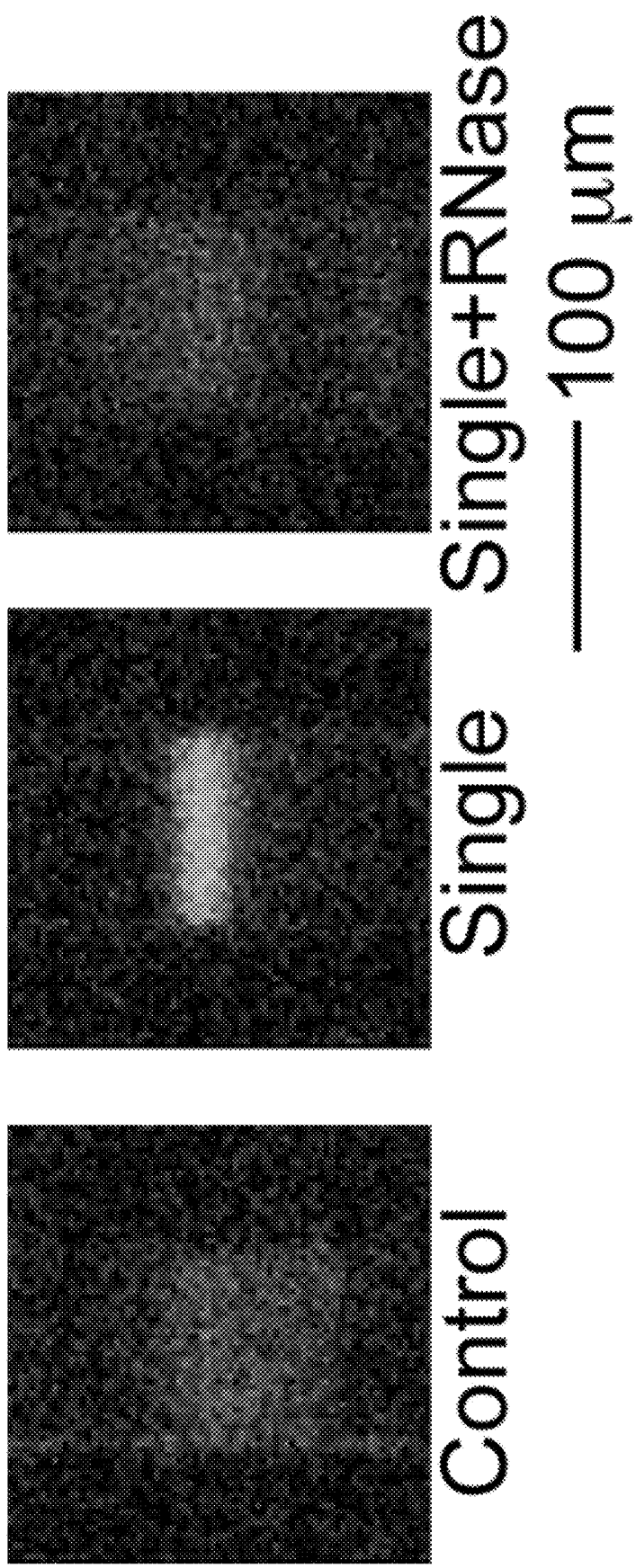
FIG. 6 shows time-resolved images of the fluorescence of the UP interface. The RNA fluorescence from the experiment with a single cell was significantly higher than that with the negative control. The fluorescence at the ITP interface approached that of no cell for the cases where we added RNase to the LE, indicating the focused and visualized molecules in the UP interface were RNA.

We confirmed our attribution of the two fluorescent regions as cell nucleus and total cytoplasmic RNA by a series of experiments using Hoechst 33342 dye (B2261, Sigma-Aldrich, which is selective for DNA versus RNA) and using RNase (RNase A, QIAGEN). First, experiments with Hoechst 33342 (and not RNase) revealed that the ITP interface showed negligible fluorescence compared to the negative control, while cell nuclei showed significant fluorescence intensity (c.f. FIG. 5). This is, of course, consistent with the cell nuclei always containing DNA and DNA was not focusing at the ITP interface. Second, we show experiments conducted with RNase mixed into the LE (see FIG. 6). With RNase, the ITP-focused zone signal reduced to values on the order of negative controls (signal-to-noise ratios, SNR, of order 0.4). These observations lend confidence to the conclusion that our method focuses cytoplasmic RNA with ITP, while leaving behind cell nuclei. Our identification of cell nuclei versus RNA was also consistent with our observations of pre- and post-lysis cell morphology, including using overlaid transmitted light and fluorescence visualizations.

S-3 Development of an Experiment Calibration Curve

Figure 7A:
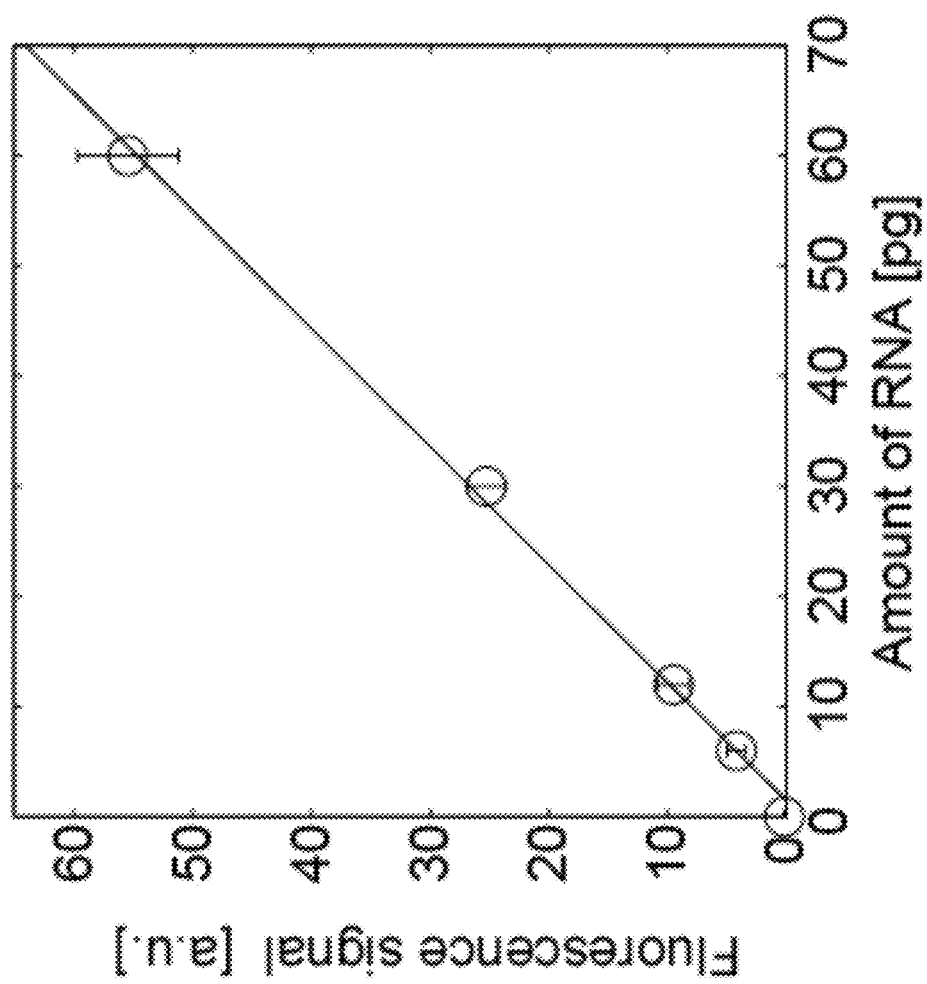
FIG. 7A shows a calibration curve for the RNA quantification. We obtained the curve as the relation between the fluorescence signal and the amount of RNA spiked into the TE in the injection channel.

We used a series of ITP experiments with spiked synthetic RNA to build a calibration curve for absolute quantitation of RNA mass. Our calibration process was similar to that used by Persat et al. (Anal. Chem. (2009) 81:9507-9511; herein incorporated by reference in its entirety). We used conditions and solutions identical to those of cell experiments, and spiked with known concentrations of an RNA ladder (0.5-10 Kb RNA Ladder, Invitrogen). We added 2 μL of the sample solution in the W reservoir and injected it into the injection channel by applying vacuum to the S reservoir. We injected all of the dispensed sample solution in the W reservoir into the microchannel, and then removed the vacuum from the S reservoir and dispensed TE solution in the W reservoir. By this method, we exchanged 12 nL of the solution in the injection channel with the sample solution. We then inserted electrodes to the W, N and E reservoirs and initiated the ITP process to focus RNA at the ITP interface. We quantified ITP peak SNR, and constructed the calibration curve shown in FIG. 7A. The standard deviation normalized by the mean for the data was about 12%. We attribute at least part of this variation to errors in fluid handling including pipetting and vacuuming The solid line shows a linear regression with coefficient $R^2$=0.98. We used this calibration curve to relate integrated fluorescence signal and absolute RNA amount in the range of 0 to 60 pg.

S-4 Image Processing of Cell Nuclei

Figures 8A, 8B:
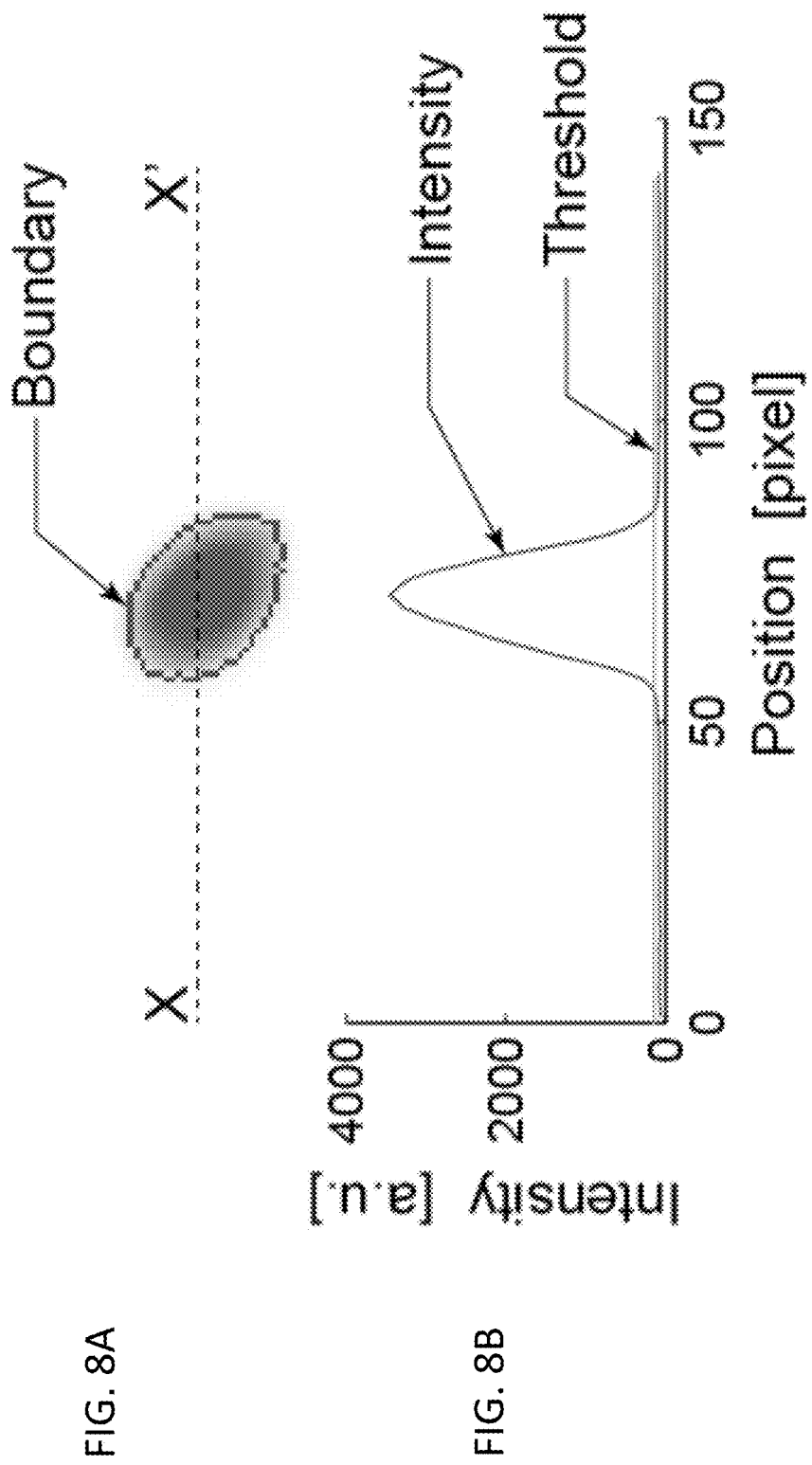
FIGS. 8A and 8B show the detection of a nucleus by image processing.

We analyzed images of the nucleus to identify their boundaries and integrate fluorescence intensity in the nucleus. To do so, for each nucleus, we set the focal plane to the highest intensity. We detected the nucleus as an area with fluorescence intensities higher than a specified threshold. To automate the threshold setting, we set the threshold value to $I_{bk}+\sigma$, where $I_{bk}$ is the mean intensity of the background fluorescence within the channel and $\sigma$ is the standard deviation of this background. The fluorescence image in FIG. 8A shows an image of a cell nucleus and the boundary determined by this threshold. FIG. 8B shows a plot of the intensity along the X-X' line. The threshold is shown in the latter plot as a straight horizontal line. The parameters of the nucleus were obtained using the function of 'regionprops' in MATLAB. We present these integrated intensity measurements of DNA in the nucleus as relative mass values and not absolute quantitation of mass. Absolute quantification of DNA inside nuclei is challenging for three reasons. First, the labeling efficiency associated with transport into the cell nucleus and the quantum yield of the dye in the cell nucleus is difficult to determine in an absolute sense. Second, obtaining a control value of the absolute DNA amount in the nucleus is difficult. This is unlike the case of free RNA focused in an ITP zone (where we can use spiked RNA focused into an ITP zone as a control). Third, we note that the integrated fluorescence intensity showed variation of about 15% as a function of the location of the focal plane within the channel depth. We hypothesize this variation is associated with the three-dimensional structure of cell nucleus.

Figure 2A:
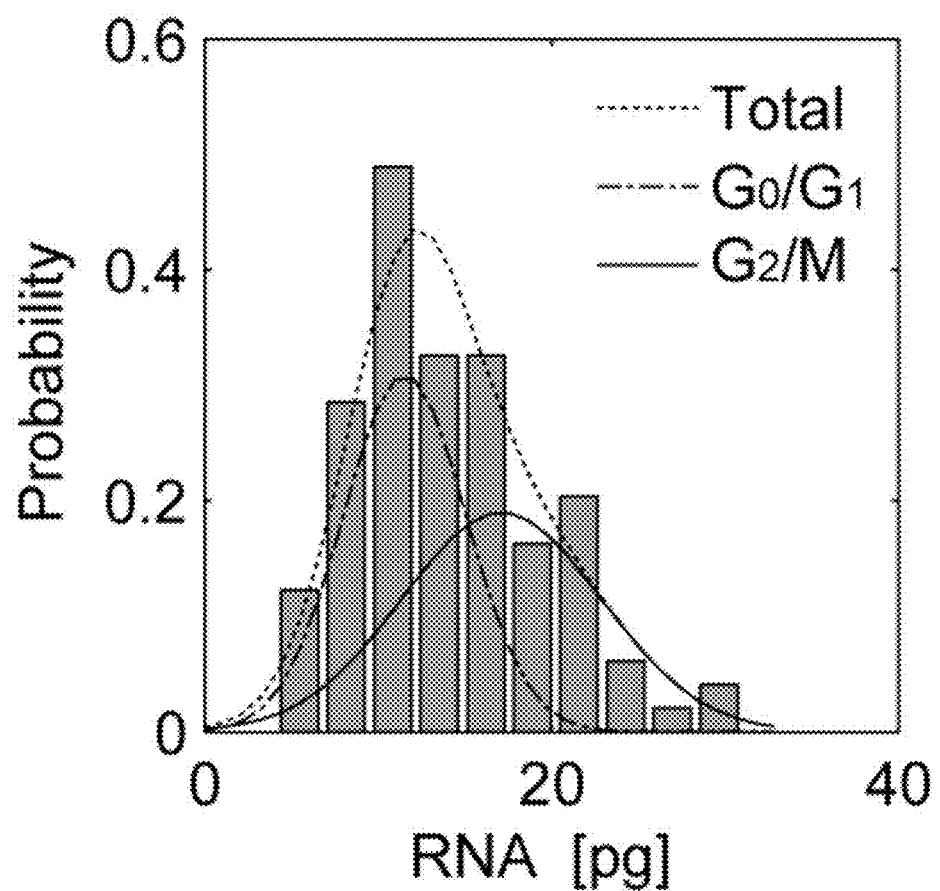
FIGS. 2A-2F show statistics on measurements of RNA and DNA from individual single cells.
Figure 2B:
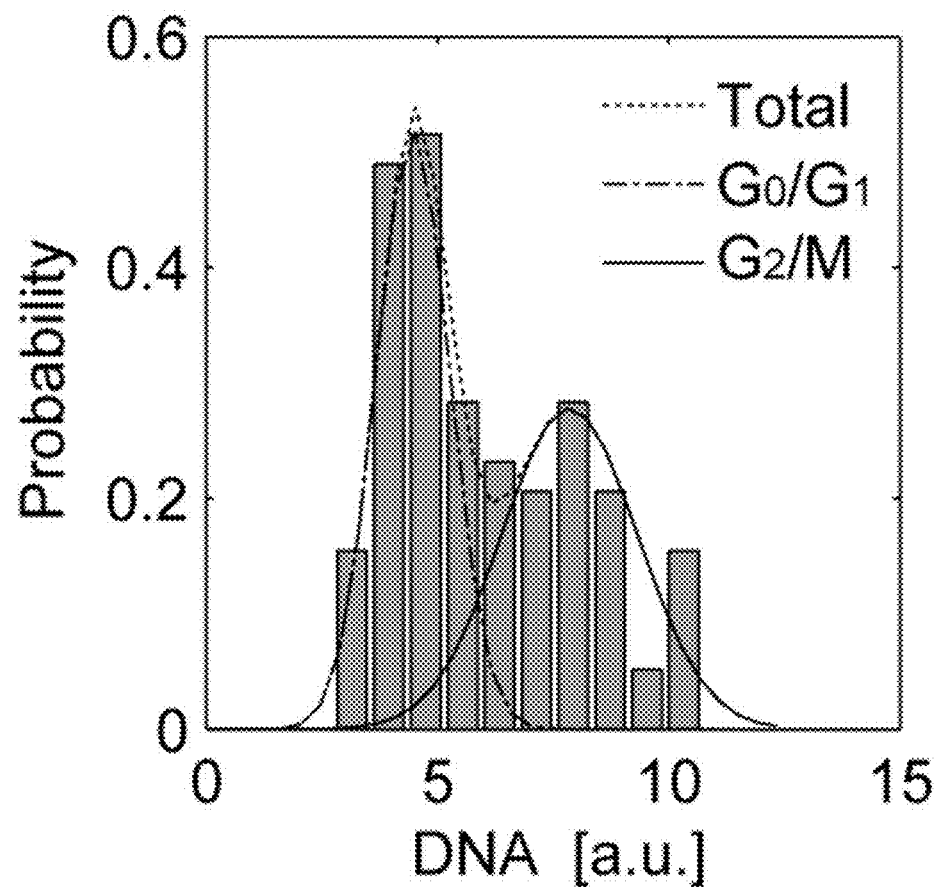
Figure 2C:
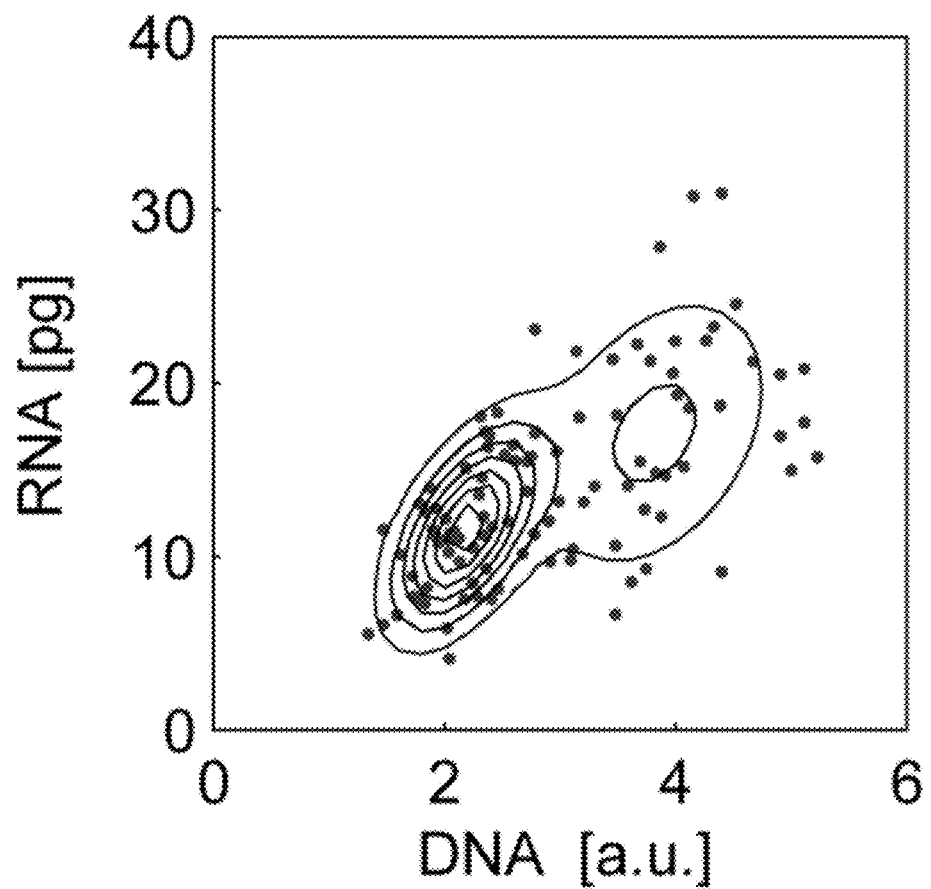

S-5 Correlation Between Absolute Amount of Extracted RNA and Relative Amount of DNA We examined the correlation between the quantified amount of extracted RNA mass and the integrated fluorescence signals of corresponding, individual cell nuclei as shown in FIG. 2C. We obtained a correlation coefficient of 0.62 ($p=5.5\times10^{-12}$ against the null hypothesis of no correlation), indicating a significant positive correlation. As we discussed in the section S-3, we obtained 12% as the coefficient of variation among experiments used to generate the calibration curve. This variation is much lower than coefficients of variation for the RNA and DNA quantifications: 39% and 34%, respectively. This strong positive correlation therefore suggests that the variation found in the amount of the extracted RNA was not due to variations in the extraction efficiency. Further these observations of positive correlation and the relative variations in calibration experiments versus cell data each support the conclusion that the observed variations in the single cell data can be attributed to biological variations and not just experimental uncertainty in the measurement.

Figure 9A:
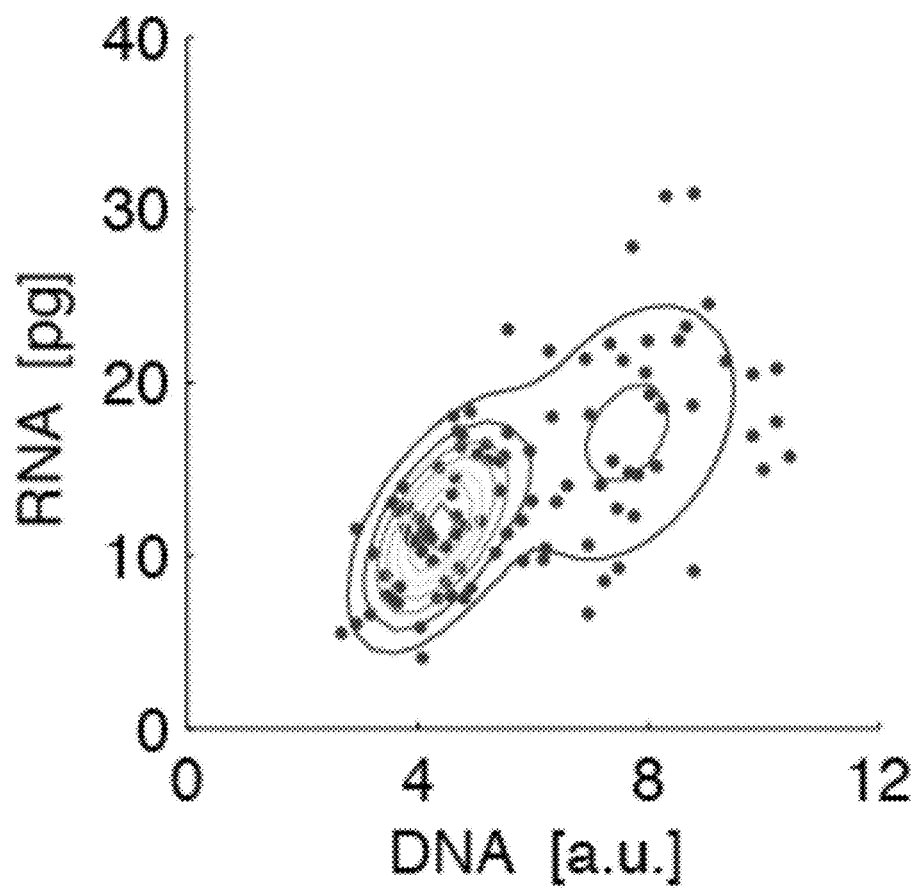
FIGS. 9A and 9B show a two-dimensional Gaussian mixture analysis of the relation between the extracted RNA amount and the fluorescence signal of the nucleus.
Figure 9B:
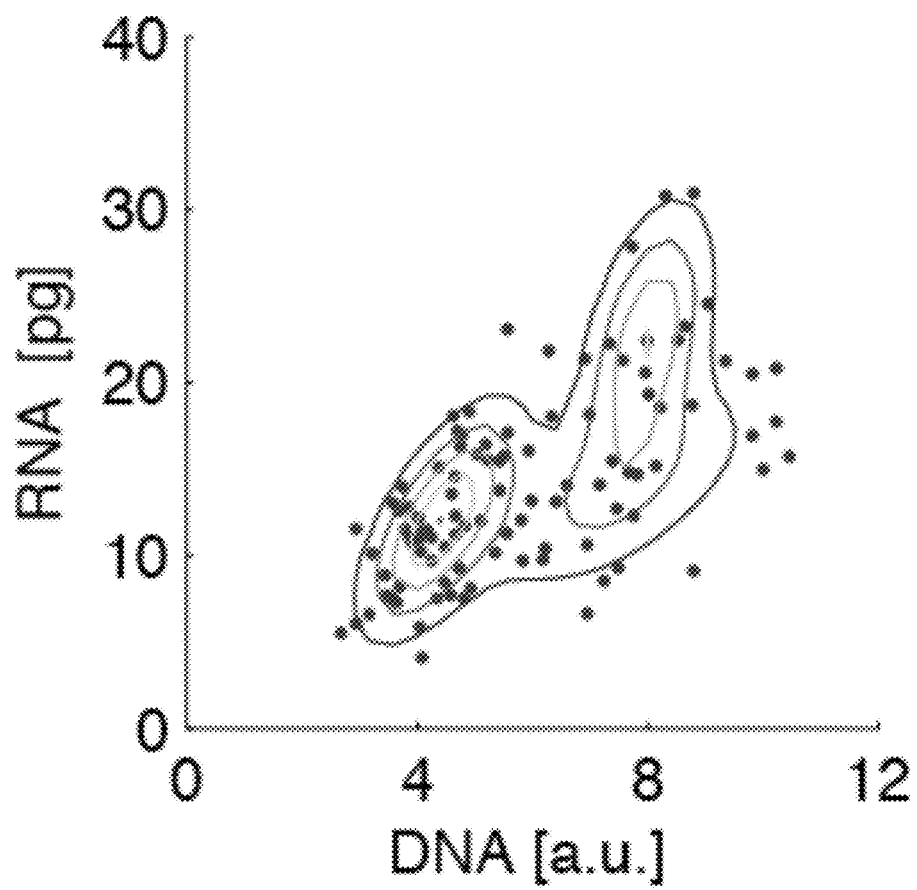

FIG. 9 shows a two-dimensional Gaussian mixture analysis of the data relating the extracted RNA amount and the relative integrated fluorescence of the nucleus. We performed this analysis using the function 'gmdistribution.fit' in MATLAB. We examined one, two, three and four two-dimensional Gaussian distributions to fit the data. We evaluated the fitting result on the basis of Akaike's information criterion (AIC) and Bayesian information criterion (BIC) values as listed in Table 1. The minimum AIC and BIC values for the two-dimensional Gaussian distribution suggested that the two Gaussian distributions provided the best fit without over-fitting of the data.

Table 1 AIC and BIC-values corresponding to fits with one, two, three, and four two-dimensional Gaussian distributions obtained from 100 single cells. The minimum values for both the AIC and BIC at two two-dimensional Gaussian suggest the two-Gaussian fit provides the best trade-off between goodness of fit and over-fitting. Fitting with three and four Gaussians resulted in over-fitting.

|  | Number of Gaussians | | | |
| --- | --- | --- | --- | --- |
|  | 1 | 2 | 3 | 4 |
| AIC-values | 527 | 494 | 499 | 505 |
| BIC-values | 540 | 523 | 543 | 565 |

Results

In the current work, we focused on a single cell assay using electric fields to control the entire process in a standard fluidic chip with no moving parts except for the use of end-channel electrodes after initial isolation of a single cell. We demonstrated controlled manipulation and lysis of a single cell. RNA from the cytoplasm of the lysed single cell was selectively extracted by ITP and quantitated. Our protocol can be used for absolute quantification of RNA and correlation analysis with semi-quantitative DNA amounts from a single cell and to assess heterogeneity in the amounts of RNA and DNA in single cells.

FIGS. 1A-1C show a schematic representation of our assay. We used an off-the-shelf microfluidic chip with a cross geometry (model NS12A, Caliper Life Sciences, CA). The microfluidic chip consists of borosilicate glass microchannels of 90 μm wide and 20 μm deep (see FIG. 3A). We prefilled the microchannel with LE buffer and added a 2 μL cell suspension (approximately 5 cells/μL) in TE buffer into the west (W) reservoir. We introduced individual cells from this low concentration solution by applying a vacuum to the south (S) reservoir. We observed a living single cell isolated in the injection channel as approximately spherical bodies with diameters ranging from 10 to 15 μm (FIG. 1D). Once we visually confirmed a single cell was isolated in the injection channel, between the W reservoir and the cross-junction, we removed the vacuum and added 20 μL of the TE buffer to the W and north (N) reservoirs. We placed platinum wire electrodes into the W, N, and east (E) reservoirs, and applied voltage to the electrodes using a high voltage sequencer (HVS448 3000D, LabSmith). We first applied a bipolar voltage pulse between the W and N reservoirs (each pulse 100 ms wide, 3000 V magnitude) to lyse the single cell. We then immediately initiated ITP by applying a DC electric field and extracted RNA from the lysed cell. The voltage sequence is shown schematically in FIG. 3B. RNA simultaneously complexes with SYBR Green II mixed homogenously into the LE and we detect it 40 mm downstream of the cross-junction.

Our injection protocol and end-channel electrodes only lysed cells placed in the injection channel (see the Supplementary Information (SI) section S-1). The cell lysing process was very repeatable and showed 100% yield across all observations.

Figure 1F:
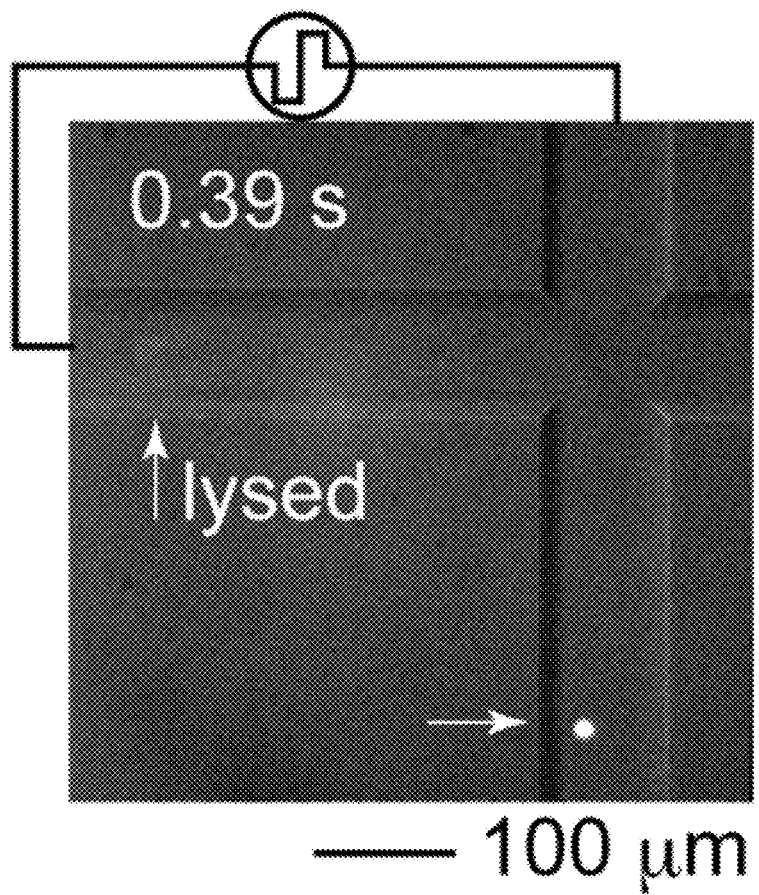

Our application of a DC electric field immediately upon completion of the lysing pulse resulted in rapid ITP focusing of the RNA from individual cells. FIG. 1F shows representative images of extracted RNA in the ITP interface from a single cell. We obtained this image 220 seconds from the time of cell lysis. We defined the signal-to-noise ratios (SNR) of the RNA fluorescence in the ITP zone as the fluorescence intensity above background divided by the standard deviation among negative controls. Our typical SNR was 7.6 and the minimum SNR was 1.5.

All experiments resulted in a focused RNA zone in ITP and a trailing ellipsoidal body we attributed to a cell nucleus (see FIG. 1F and also SI section S-2). The nuclei migrated in the same direction as the ITP interface, indicating a net negative charge, but the drift velocity of the nuclei varied significantly among experimental runs. We attribute this variation to variations in size and morphology, and other differences (e.g., number and ionization states of surface proteins). In contrast, the ITP-focused zone always remained in motion at drift velocities expected from the ITP dynamics (Crissman et al. (2003) Anal. Chem. 75:5646-5655).

Figure 7B:
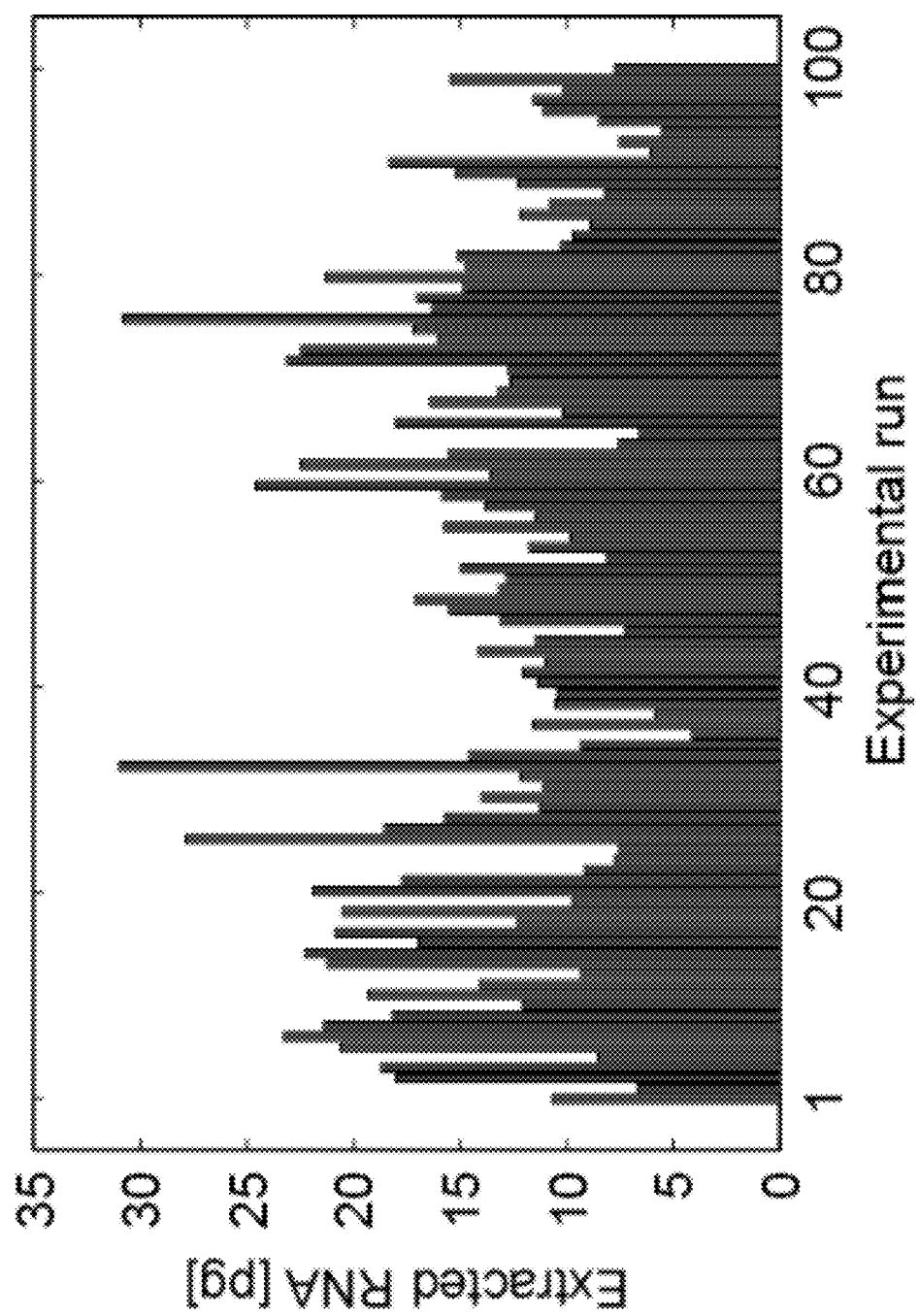
FIG. 7B shows the amount of RNA extracted from 100 single cells in chronological order.

We performed 100 experiments where we lysed single cells, separated nuclei from total cytoplasmic RNA, focused and quantified cytoplasmic RNA, and obtained relative measures of total DNA in individual nuclei. We used a calibration curve constructed using experiments with spiked synthetic RNA (0.5-10 Kb RNA Ladder, Invitrogen) to quantify the absolute amount of RNA in the ITP interface using integrated intensity (see the SI section S-3). FIG. 2A shows a histogram for measured absolute RNA masses. See also FIG. 7B for RNA data ordered chronologically versus experimental run. The histogram showed a most frequent value of about 11.0 pg, and the mean was 14.1 pg. These measures are consistent with reported total RNA from single mammalian cells (Wen et al. (2008) Anal. Chem. 80:6472-6479). The standard deviation normalized by the mean value was 39% (significantly larger than the 12% value observed among runs in the calibration data, see the SI section S-3). The magnitude of the variation relative to variation within repeats of the calibration leads us to conclude that the large observed variation in our cell data is due to cell population heterogeneity (see further discussion below).

In all of these experiments, we integrated the fluorescence intensity of the cell nucleus as an additional, correlated measurement specific to each cell (see the details of the image analysis in the SI section S-4). As we discussed in SI section S-2, we confirmed our protocol extracts only cytoplasmic RNA from the lysed cell and keeps DNA in the nucleus. The integrated fluorescence intensity from the cell nucleus provides a measure of relative amount of DNA in a single cell. The relative amount of DNA also showed large variation with a standard deviation normalized by mean of 34% (significantly larger than estimated measurement uncertainties, see FIG. 2B). The DNA amount distribution showed two distinct peaks: The first at about 4.5 a.u. and the second at about 7.8 a.u. (1.7 ratio of the local maxima). We attributed these two peaks to the G0/G1 and G2/M cell phases,[30] where single cells contain single and double copies of DNA, respectively. We hypothesize that the ratio between local maxima in the histogram was smaller than 2 because of the contribution by S phase, where the cells synthesize DNA.

We examined the correlation between the absolute amount of the RNA and the relative amount of DNA as shown in FIG. 2C. We observed a significant correlation with a positive coefficient of 0.62 (a p value of $5.5 \times 10^{-12}$ for the null hypothesis of no observed correlation). The positive coefficient indicates that the greater amount of DNA coincides with the greater amount of the RNA. We thus attributed the variation in each measure to the cell cycle, but not to the extraction efficiency of RNA. See also the SI Section S-5 for more details.

We also performed an analysis based on the fitting of two-dimensional Gaussian distributions to the data in FIG. 2C. We observed the best fitting result with two two-dimensional Gaussians, suggesting that the 100 single cells originated from two distinct populations (see also the SI Section S-5). We showed the projection of the two-dimensional fitting as lines in FIGS. 2A and 2B. In FIG. 2B, we found that each population captures the two distinct peaks, respectively. This supports the conclusion that we observed two distinct populations associated with the G0/G1 and G2/M phases. We also observed a consistent fitting result for the amount of extracted RNA, as shown in FIG. 2A.

Figure 2D:
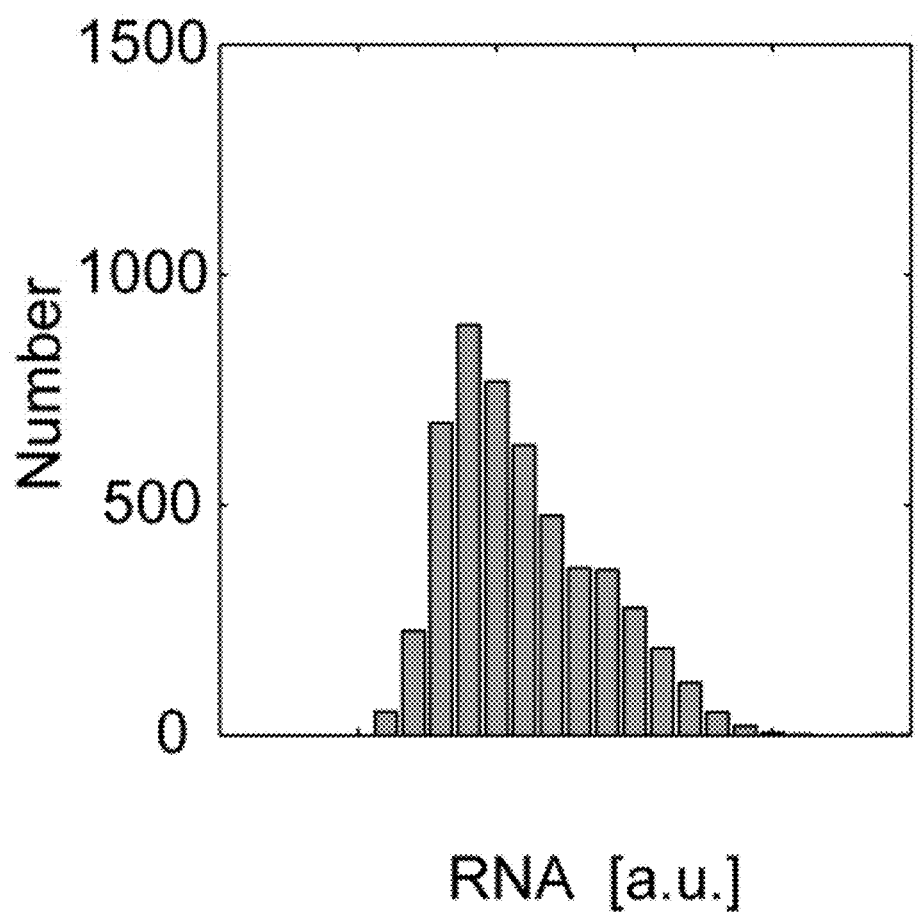
Figure 2E:
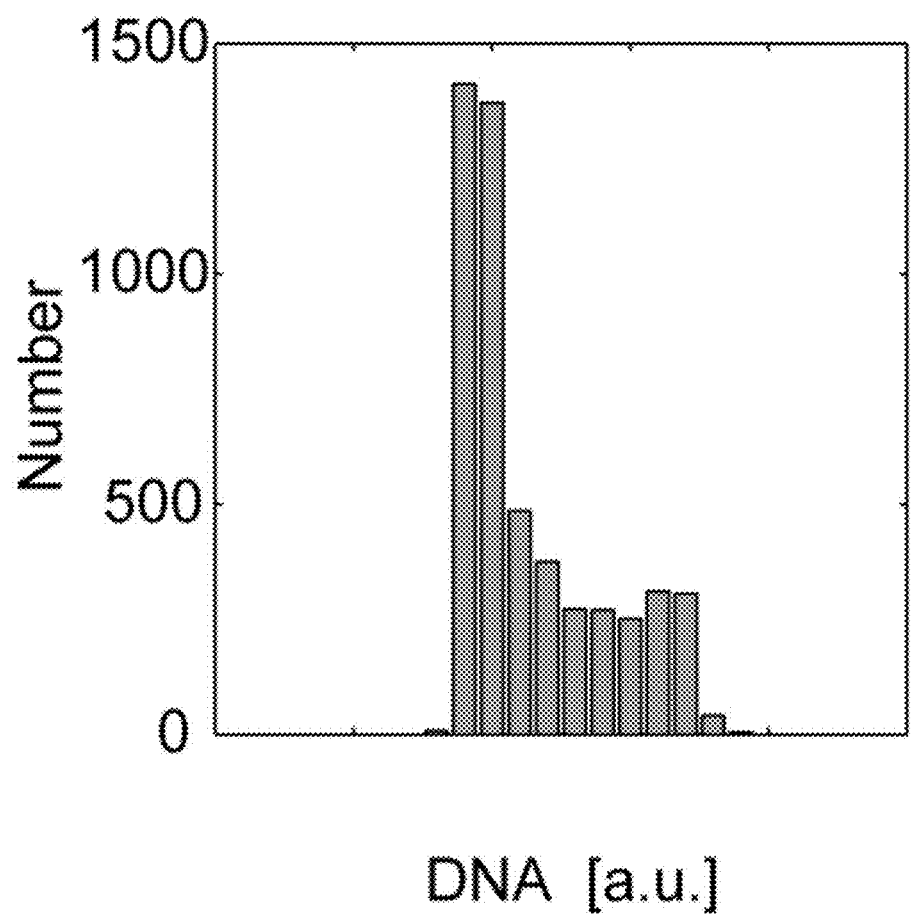
Figure 2F:
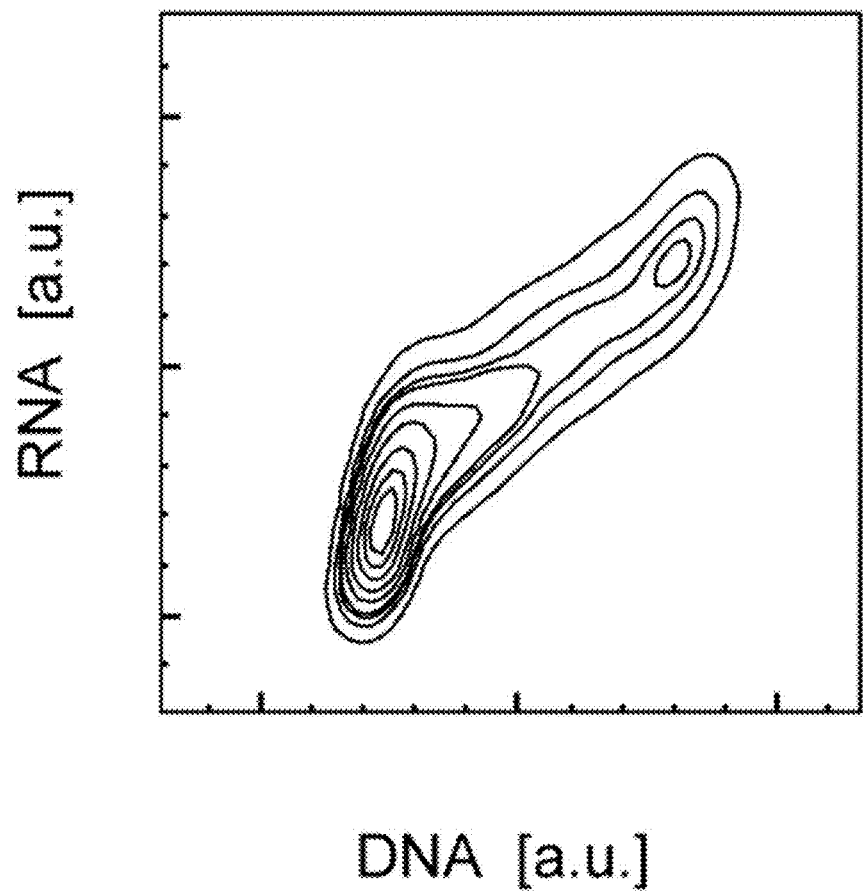

We further evaluated our technique by performing analysis on cells from the same cell culture with a fluorescence activated cell sorter (FACS). We used a protocol using Pyronin Y and Hoechst 33342 fluorescent dyes (Gao et al. (2004) Lab on a Chip 4:47-52) for RNA and DNA relative quantification, respectively. We summarize the FACS analysis in FIGS. 2D-2F. We observed good qualitative agreement between our assay and FACS. We found that the measurements of relative RNA and relative DNA amounts provided by FACS also showed correlated, bimodal distributions, as with our data. The correlation diagram of FIG. 2F was obtained from 5109 cells, and so showed more details than our assay. FACS is a mature, high-throughput technique and so offers a much larger number of measurements. However, unlike FACS, our assay provides absolute quantitation of RNA and further physically lyses and separates DNA from RNA on chip. The latter is advantageous for integration with downstream analysis such as CE and cDNA hybridization based assay (Bahga et al. (2011) Anal. Chem. 83:6154-6162; Eid et al. (2013) Analyst 138:3117-3120; Garcia-Schwarz & Santiago (2013) Angew. Chem. Int. Ed. Engl. 52(44):11534-11537). In contrast, the relative DNA and relative RNA quantities obtained with FACS cannot be preserved, fractionated, and made available for individual analyses. We hope to further automate our method in the future to increase the number of cells analyzed and integrate further downstream correlated analyses.

In summary, we developed an electrokinetic method for rapid and selective cell lysing, separation of cytoplasmic RNA from nuclear DNA; collection, focusing, and absolute quantification of RNA; and simultaneous relative quantification of DNA from living single cells. Unlike FACS, our technique obtains absolute RNA quantitation and physically lyses and separates RNA from DNA. The approach also creates the opportunity to fractionate and deliver DNA and RNA to other downstream correlated analyses. We hope to demonstrate such additional integration and automate our assay to include full electric field control of cells, RNA, and nuclei; and image-analysis-based cell identification and control.

While the preferred embodiments of the invention have been illustrated and described, it will be appreciated that various changes can be made therein without departing from the spirit and scope of the invention.

What is claimed is:

1. A method of preparing cytoplasmic and nuclear nucleic acids from a cell, the method comprising:
   a) isolating a cell in a fluidic channel having fluid therein;
   b) applying an electric field to the fluidic channel with the isolated cell therein, wherein the plasma membrane of the cell is disrupted without lysing the nuclear membrane; and
   c) performing isotachophoresis (ITP) on the contents of the cell within the fluidic channel having the fluid therein by:
      i) using a trailing electrolyte (TE) and a leading electrolyte (LE), wherein cytoplasmic nucleic acid is concentrated at the LE-TE interface, and
      ii) retarding the nucleus to cause nucleic acid from the cytoplasm ("cytoplasmic nucleic acid") to be separated from nucleic acid contained in the nucleus ("nuclear nucleic acid").

2. The method of claim 1, wherein the electric field is applied between reservoirs that are in fluidic communication with the fluidic channel and includes a bipolar voltage pulse that selectively disrupts the plasma membrane of the cell, without lysing or while preserving integrity of the nuclear membrane.

3. The method of claim 2, wherein the duration of each individual pulse is about 100 milliseconds and performing ITP on the contents of the cell includes applying the other electric field to the fluidic channel and between the reservoirs by switching from the bipolar voltage pulse to direct current voltages.

4. The method of claim 2, wherein the potential induced across the plasma membrane of the isolated cell is about 3 volts.

5. The method of claim 2, wherein the electric field in the fluidic channel is about 270 kV/m.

6. The method of claim 1, wherein the fluidic channel includes at least a first fluidic channel and another, second fluidic channel connected at a junction, wherein each fluidic channel has a first end connected to a first reservoir and a second end connected to a second reservoir, wherein applying the electrical field includes applying voltage pulses between the first reservoir and the second reservoir and performing electrical lysis on the isolated cell, further comprising removing cell debris from the cytoplasmic nucleic acid.

7. The method of claim 1, wherein applying the electric field to the fluidic channel and performing ITP further includes applying a voltage sequence including:
   the electric field which generates a bipolar voltage pulse that disrupts the plasma membrane of the isolated cell
   another electric field which generates direct current voltages to initiate performance of ITP; and
   further comprising removing the nucleus after ITP.

8. The method of claim 1, wherein the method is performed in a microfluidic device having the fluidic channel and reservoirs coupled to the fluidic channel, the method further including removing the cytoplasmic nucleic acid from the LE-TE interface, wherein the electric field includes a voltage sequence applied to the reservoirs and includes two bipolar voltages applied to disrupt the cell followed by a direct current voltage that is then applied to the reservoirs for initiating ITP and extracting RNA.

9. The method of claim 1, wherein applying the electric field to the fluidic channel and performing ITP further includes applying a voltage sequence including the electric field and another electric field for initiating ITP, and further comprising lysing the nuclear membrane of the nucleus.

10. The method of claim 9, wherein the method is performed in a microfluidic device having the fluidic channel and the electric field is selectively applied to the fluidic channel as opposed to another location of the microfluidic device, wherein lysing the nuclear membrane is performed using a chemical, mechanical, electrical, or thermal lysing method.

11. The method of claim 1, further comprising adding a detectable label to the cytoplasmic nucleic acid or nuclear nucleic acid.

12. The method of claim 11, wherein the detectable label is a fluorescent dye.

13. The method of claim 1, further comprising quantifying the amount of cytoplasmic nucleic acid.

14. The method of claim 1, further comprising quantifying the amount of nuclear nucleic acid.

15. The method of claim 1, wherein retarding the nucleus to cause cytoplasmic nucleic acid to be separated from nuclear nucleic acid of cell further includes using a sieving matrix that retards the nucleus, where the sieving matrix comprises a block copolymer, a linear polymer, or a cross-linked polymer.

16. The method of claim 1, wherein retarding the nucleus to cause cytoplasmic nucleic acid to be separated from nuclear nucleic acid of the cell further includes using a sieving matrix that retards the nucleus, wherein the sieving matrix comprises polyvinylpyrrolidone (PVP).

17. The method of claim 16, wherein the concentration of PVP is greater than 0.2%.

18. The method of claim 17, wherein the concentration of PVP is about 0.4%.

19. The method of claim 1, further comprising adding an agent for suppressing electroosmotic flow in the fluidic channel.

20. The method of claim 19, wherein the agent for suppressing electroosmotic flow is selected from the group consisting of polylactams, substituted polyacrylamide derivatives, water soluble methylhydroxyethyl derivatives of cellulose, polyvinylalcohol, polyvinylpyrrolidones, and polyethyleneglycols.

21. The method of claim 20, wherein the polylactam is polyvinylpyrrolidone.

22. The method of claim 1, wherein comprising adding an osmotic agent to compensate for differences in osmotic pressure between intracellular and extracellular media.

23. The method of claim 22, wherein the osmotic agent is sucrose.

24. The method of claim 1, wherein ITP is performed with a solution containing the LE comprising tris(hydroxymethyl)aminomethane (Tris) and hydrogen chloride (HCL).

25. The method of claim 1, wherein ITP is performed with a solution containing the TE comprising tris(hydroxymethyl)aminomethane (Tris) and 4-(2-hydroxyethyl)-1-piperazineethanesulfonic acid (HEPES).

26. The method of claim 1, wherein the LE and TE are contained in a solution at a pH between 4 and 10.

27. The method of claim 26, wherein the pH is between about 8.0 and about 8.3.

28. The method of claim 1, further comprising amplifying at least one RNA or DNA.

29. The method of claim 1, further comprising isolating at least one RNA or DNA.

30. The method of claim 1, further comprising separating RNA or DNA molecules by an electric field-based method.

31. The method of claim 30, wherein the electric field-based method is selected from the group consisting of polyacrylamide gel electrophoresis, agarose gel electrophoresis, capillary electrophoresis, and pulsed field electrophoresis.

32. The method of claim 1, wherein the method is performed in a microfluidic device comprising the fluidic channel.

33. The method of claim 32, wherein the fluidic channel includes at least a first fluidic channel and a second fluidic channel connected at a junction, wherein each fluidic channel has a first end connected to a first reservoir and a second end connected to a second reservoir.

34. The method of claim 33, wherein the first fluidic channel divides at least one channel branch point into two or more channels, wherein the nucleus and cytoplasmic nucleic acids are distributed to separate channels.

35. The method of claim 33, wherein retarding the nucleus to cause cytoplasmic nucleic acid to be separated from nuclear nucleic acid of the cell further includes using a sieving matrix that retards the nucleus, the method further comprising:
 a) filling the first channel with a solution comprising the leading electrolyte and the sieving matrix;
 b) isolating the cell in the first channel by introducing the sample comprising the cells into the first reservoir of the first channel and applying a vacuum at a reservoir of the second channel to move the cell into the first channel, thereby isolating the cell;
 c) applying an electric field across the first channel in the vicinity of the cell, whereby the plasma membrane of the cell is disrupted without lysing the nuclear membrane;
 d) adding trailing electrolyte to the first reservoir of the first channel; and
 e) performing isotachophoresis (ITP) on the contents of the cell in the first channel.

36. The method of claim 35, further comprising delivery of the nucleus and cytoplasmic nucleic acids to separate locations in the microfluidic device via at least one channel branch point into two or more channels.

37. The method of claim 36, wherein the nucleus and cytoplasmic nucleic acids are distributed to separate reservoirs or channels within the microfluidic device.

38. A method of preparing nuclear RNA and cytoplasmic RNA from a cell, the method comprising:
 a) isolating the cell in a fluidic channel having fluid therein;
 b) applying an electric field to the fluidic channel with the isolated cell therein, whereby the plasma membrane of the cell is disrupted without lysing the nuclear membrane; and
 c) performing isotachophoresis (ITP) on the contents of the cell while the cell is within the fluidic channel by:
  i) using a trailing electrolyte (TE) and a leading electrolyte (LE), wherein cytoplasmic RNA is concentrated at the LE-TE interface, and
  ii) retarding the nucleus to cause RNA from the cytoplasm ("cytoplasmic RNA") to be separated from the nuclear RNA contained in the nucleus.

39. The method of claim 38, further comprising isolating nuclear RNA from the nucleus, and wherein the electric field includes a bipolar voltage pulse applied between reservoirs coupled to the fluidic channel, wherein cytoplasmic RNA migrates out of the cell.

40. The method of claim 38, further comprising isolating nuclear RNA from nuclear DNA.

41. The method of claim 40, comprising digesting the DNA enzymatically with a deoxyribonuclease.

42. The method of claim 38, wherein the method is performed in a microfluidic device comprising the fluidic channel.

43. The method of claim 42, further comprising delivery of the nucleus and cytoplasmic RNA to separate locations in the microfluidic device.

44. The method of claim 43, wherein the nucleus and cytoplasmic RNA are distributed to separate reservoirs or channels within the microfluidic device.

45. The method of claim 38, wherein retarding the nucleus to cause cytoplasmic RNA to be separated from nuclear DNA of the cell further includes using a sieving matrix that retards the nucleus, where the sieving matrix comprises a block copolymer, a linear polymer, or a cross-linked polymer.

46. The method of claim 38, wherein retarding the nucleus to cause cytoplasmic RNA to be separated from nuclear DNA of the cell further includes using a sieving matrix that retards the nucleus, wherein the sieving matrix comprises polyvinylpyrrolidone (PVP).

47. The method of claim 46, wherein the concentration of PVP is greater than 0.2%.

48. The method of claim 47, wherein the concentration of PVP is about 0.4%.

49. The method of claim 38, further comprising adding an agent for suppressing electroosmotic flow in the fluidic channel.

50. The method of claim 49, wherein the agent for suppressing electroosmotic flow is selected from the group consisting of polylactams, substituted polyacrylamide derivatives, water soluble methylhydroxyethyl derivatives of cellulose, polyvinylalcohol, polyvinylpyrrolidones, and polyethyleneglycols.

51. The method of claim 50, wherein the polylactam is polyvinylpyrrolidone.

52. The method of claim 38, further comprising adding an osmotic agent to compensate for differences in osmotic pressure between intracellular and extracellular media.

53. The method of claim 52, wherein the osmotic agent is sucrose.

54. The method of claim 38, wherein ITP is performed with a solution containing the LE comprising Tris and HCl.

55. The method of claim 38, wherein ITP is performed with a solution containing the TE comprising Tris and HEPES.

56. The method of claim 38, wherein the LE and TE are contained in a solution at a pH between 4 and 10.

57. The method of claim 56, wherein the pH is between about 8.0 and about 8.3.

58. The method of claim 1, wherein retarding the nucleus to cause cytoplasmic nucleic acid to be separated from nuclear nucleic acid of the cell further includes using a sieving matrix that retards the nucleus.

59. The method of claim 38, wherein retarding the nucleus to cause cytoplasmic RNA to be separated from nuclear DNA of the cell further includes using a sieving matrix that retards the nucleus.

* * * * *